United States Patent [19]

Newton

[11] Patent Number: 5,525,494
[45] Date of Patent: Jun. 11, 1996

[54] AMPLIFICATION PROCESSES

[75] Inventor: Clive R. Newton, Nr Northwich, England

[73] Assignee: Zeneca Limited, London, United Kingdom

[21] Appl. No.: 200,296

[22] Filed: Feb. 23, 1994

Related U.S. Application Data

[63] Continuation of Ser. No. 571,926, Aug. 24, 1990, abandoned.

[30] Foreign Application Priority Data

Sep. 6, 1989 [GB] United Kingdom ............... 8920097

[51] Int. Cl.$^6$ ............................... C12P 19/34; C07H 21/04
[52] U.S. Cl. ........................................ 435/91.2; 536/24.33
[58] Field of Search ........................ 435/91.2; 536/24.33

[56] References Cited

U.S. PATENT DOCUMENTS

| 4,683,195 | 7/1987 | Mullis et al. ................................ 435/6 |
| 4,683,202 | 7/1987 | Mullis . | |

FOREIGN PATENT DOCUMENTS

| 0237362 | 9/1987 | European Pat. Off. . |
| 2202328 | 9/1988 | United Kingdom . |
| 2221909 | 2/1990 | United Kingdom . |
| 9011372 | 10/1990 | WIPO . |

OTHER PUBLICATIONS

Agr. Biol. Chem. 36: 1651–1653 (1972).
Nucl. Acid Res. 12: 4539–4557 (1984).
Nucl. Acid Res. 17: 2503–2516 (1989).
Scharf et al, "Direct Cloning and Sequence Analysis of Enzymatically Amplified Genomic Sequences", Science, vol. , Sep. 5, 1986, pp. 1076–1078.
Stoflet et al, "Genomic Amplification with Transcript Sequencing", Science, vol. 239, Jan. 1988, pp. 491–494.
Keller et al, "Detection of Hepatitis B Virus DNA in Serum by Polymerase Chain Reaction Amplification and Microtiter Sandwich Hybridization", Journal of Clinical Microbiology, Jun. 1990, pp. 1411–1416.
Kemp et al, "Colorimetric Detection of Specific DNA Segments Amplified by Polymerase Chain Reactions", Proc. Natl Acad Sci USA, vol. 86, pp. 2423–2427, Apr. 1989.
Syvanen, et al, "Fast quantification of Nucleic Acid Hybrids by Affinity–Based Hybrid Collection", Nucleic Acids Research, vol. 14, No. 12, 1986, pp. 5037–5048.
Syvanen et al, "Quantification of Polymerase Chain Reaction Products by Affinity–Based Hybrid Collection", Nucleic Acids Research, vol. 16, No. 23, 1988.
Saiki et al, "Genetic analysis of amplified DNA with Immobilized Sequence–Specific Oligonucleotide Probes", Proc. Natl. Acad. Sci. USA, vol. 86, pp. 6230–6234, Aug. 1989, Genetics.
Ng et al, "Recognition and Binding of Template–Primers Containing Defined Abasic Sites by Drosophila DNA Polymerase α Holoenzyme", The Journal of Biological Chemistry, vol. 264, No. 22, Aug. 5, pp. 13018–13023, 1989.
Sanger et al, Proc. Natl. Acad. Sci USA, vol. 74, No. 12, Dec. 1977, pp. 5463–5467.

*Primary Examiner*—George C. Elliott
*Attorney, Agent, or Firm*—Cushman Darby & Cushman

[57] ABSTRACT

The present invention relates to a method for the amplification of a target nucleotide sequence using a first primer comprising 1) a target binding nucleotide moiety which is substantially complementary to the desired portion of the target nucleotide sequence; and 2) a polynucleotide tail. The first primer is such that while an extension product thereof may itself serve as a template for primer extension to form an amplification primer extension product, formation of an amplification primer extension product comprising a sequence complementary to the polynucleotide tail is inhibited.

15 Claims, 4 Drawing Sheets

1 2 3 4 5 6 7

A

B 1 2 3

AMPLIFICATION PROCESSES

This is a continuation of application Ser. No. 07/571,926, filed Aug. 24, 1990, which was abandoned upon the filing hereof.

The present invention relates to amplification processes, primers for use in such processes and kits comprising such primers. In particular the invention relates to processes for preparing amplification products having a polynucleotide tail, which tail may for example be employed for solid phase capture or for linkage to a labelling or signalling system. The present invention also relates to primers for use in the amplification processes of the invention and to kits for performing such processes.

Processes for amplifying a desired specific nucleic acid sequence are known and have been described in the literature. K. Kleppe et al in J. Mol. Biol., (1971), 56, 341–361 disclose a method for the amplification of a desired DNA sequence. The method involves denaturation of a DNA duplex to form single strands. The denaturation step is carried out in the presence of a sufficiently large excess of two nucleic acid primers which hybridise to regions adjacent to the desired DNA sequence. Upon cooling two structures are obtained each containing the full length of the template strand appropriately complexed with primer. DNA polymerase and a sufficient amount of each required nucleoside triphosphate are added whereby two molecules of the original duplex are obtained. The above cycle of denaturation, primer addition and extension are repeated until the appropriate number of copies of the desired DNA sequence is obtained. It is indicated that adjustment of the primer concentration may be required.

The above method is now referred to as polymerase chain reaction (PCR) as claimed in U.S. Pat. Nos. 4,683,195 and 4,683,202 wherein amplification of a given nucleic acid sequence on a template is effected by extension of a nucleic acid primer in the presence of *Thermus aquaticus* (Taq) DNA polymerase or the Klenow fragment of *E. coli* DNA polymerase I. The amplification procedure is generally repeated for up to about 50 cycles. The examples provided only relate to short DNA sequences, generally of a few hundred base pairs.

Amplification processes such as the PCR reaction provide a useful tool for amplifying nucleic acid sequences, but it is commonly desirable that the amplified product be capable of attachment to a further species for example for capture or signalling purposes. The further species may therefore be for example a solid phase or signalling moiety. Thus for example it may be desirable to isolate the amplified product, for example as a purification step in the production of nucleotide probes or as a quality control step in their production or in assay methods such as for example in the diagnosis of genetic disorders. It may also be desirable to label or mark, or augment the label or marker associated with or carried by the amplified product.

In order to render the amplified product capable of attachment to a further species the primer(s) used for amplification may for example carry an antibody or antigen, for example, for capture onto a solid phase carrying corresponding antigen or antibody, but such an antibody and antigen would need to be thermostable to withstand PCR temperature cycling. An alternative technique would be to use a primer carrying one member of a complex forming pair such as biotin, the further species carrying the other member of the complex forming pair such as avidin. Such techniques tend to be unsatisfactory because these techniques inter alia, are not readily adaptable to the simultaneous performance of more than one test. An assay in which attachment of the amplified product to the further species was based on nucleic acid hybridisation would overcome at least in part the above-identified problems but if a primer for a PCR reaction were provided with a polynucleotide tail, for example for binding to solid phase immobilised DNA, the Taq DNA polymerase present would cause amplification of the polynucleotide tail as well as the extended target binding portion of the primer. In such a case, where the polynucleotide tail is itself amplified, competition for attachment to the further species (for example to a solid phase or signalling moiety) arises which thereby inhibits binding. The present invention is based on the discovery that the above-identified problems may be overcome, at least in part, if the amplification process is effected using a first primer comprising 1) a target binding nucleotide moiety which is substantially complementary to the desired portion of the target nucleotide sequence; and 2) a polynucleotide tail; the first primer being such that whilst an extension product thereof may itself serve as a template for primer extension to form an amplification primer extension product, formation of an amplification primer extension product comprising a sequence complementary to the polynucleotide tail is inhibited.

Thus according to one feature of the present invention there is provided a method for the amplification of a target nucleotide sequence, which method comprises contacting the target nucleotide sequence under hybridising conditions, together or sequentially, with a first primer for a desired portion thereof, a corresponding amplification primer, appropriate nucleotides and an agent for polymerisation of the nucleotides the first primer comprising:

1) a target binding nucleotide moiety which is substantially complementary to the desired portion of the target nucleotide sequence; and 2) a polynucleotide tail;

such that the first primer may be subjected to primer extension whereby a first primer extension product is synthesised based on the target polynucleotide sequence as template, and after denaturation of the first primer extension product from its template and hybridisation of the amplification primer to the desired portion of the first primer extension product, primer extension may be effected to form an amplification primer extension product, the presence of the first primer in the first primer extension product being effective to inhibit formation of a sequence complementary to the polynucleotide tail in the amplification primer extension product.

It will be appreciated that the steps of separating primer extension product (whether the extension product be first primer extension product or amplification primer extension product) from its template and contacting the single stranded molecules thus obtained with first primer and amplification primer under conditions such that further primer extension products are synthesised may be repeated as many times as necessary to obtain the desired level of sequence amplification.

The first primer may if desired comprise the target binding nucleotide moiety and the polynucleotide tail with a nucleotide polymerisation blocking moiety therebetween. The presence of a nucleotide polymerisation blocking moiety is not however essential since the agent for polymerisation may be inhibited from forming an extension product based on the polynucleotide tail as template for example if more than one polynucleotide tail is bonded to the target binding nucleotide moiety or for example if the target binding nucleotide moiety and the polynucleotide tail are linked to one another but the moiety and the tail are in the opposite sense to one another, the target binding nucleotide moiety generally being in the 5'—→3' sense and the polynucleotide tail being therefore generally in the 3'—→5' sense, with linkage via their 5' termini.

If desired the amplification primer may, in addition to the first primer, comprise:
1) a target binding nucleotide moiety which is substantially complementary to the desired portion of the target nucleotide sequence; and
2) a polynucleotide tail;

such that the amplification primer may be subjected to primer extension whereby an amplification primer extension product is synthesised based on the first primer extension product as template, and after denaturation of the amplification primer extension product from its template and hybridisation of the first primer to the desired portion of the amplification primer extension product, primer extension may be effected to form a first primer extension product, the presence of the amplification primer in the amplification primer extension product being effective to inhibit formation of a sequence complementary to the polynucleotide tail in the first primer extension product.

As stated in relation to the first primer, a nucleotide polymerisation blocking moiety may if desired be positioned between the target binding nucleotide moiety and the polynucleotide tail although this not necessary.

The method of the present invention may, for example, be employed to capture amplified product for example on to solid phase and/or to bind the amplified product to label or marker, regardless of whether the amplified product itself carries a label or marker. Thus the method of the present invention enables the signal associated with an amplified product to be enhanced and moreover renders an amplified product capable of detection and/or capture on to solid phase by any convenient technique such as for example techniques as described in European Patent Publication Nos. 79,139; 124,221; 128,332; 153,873; 185,494; 204,510; or 225,807 as described in U.K. Patent Publication Nos. 2,019,408 or 2,169,403 or as described in PCT Patent Publications WO87/03622 or WO88/02785. Furthermore the method of the present invention enables more than one amplification product to be identified in a single test by appropriate design of the polynucleotide tail. Thus for example the polynucleotide tail of a primer in respect of a first locus may be distinguishable from the polynucleotide tail in respect of a further locus or loci such that amplified product in respect of the first locus may for example be captured onto a first and distinguishable solid phase whilst amplified product(s) in respect of a further locus or loci are captured on one or more further solid phase(s) which solid phases are preferably distinguishable from one another. Similarly if desired, amplified product in respect of a first locus may be distinguishably labelled or marked via the primer's polynucleotide tail whilst amplified product(s) in respect of a further locus or loci may also be labelled or marked preferably such that amplified product in respect of each locus may be distinguished by a different label or marker. Thus for example the polynucleotide tail may be employed to match a given signal to a given locus.

The method of the present invention may also be effected in the solution phase, conveniently using an oligonucleotide primer which is essentialy complementary to the 3'end of the non-amplifiable tail primer as far as the nucleotide polymerisation blocking moiety and which is for example conjugated to a hapten capable of isolating unincorporated non-amplifiable tail primer. The prefered hapten is a magnetic bead. After contacting the reaction mixture with the hapten conjugated oligonucleotide and placing this for example in a magnetic field, the unincorporated non-amplifiable tail primer is retained, preferably within a microtitre dish well. The reaction mixture including unincorporated non-amplifiable tail primers is then further contacted under hybridising conditions with a detection primer conjugated, for example, to a fluorophore. Any convenient fluorophore may be used, such as fluorescein and rhodamine, for example fluorescein. The presence of the amplified product may then be detected for example by fluorescence polarisation according to the methods described in our European Patent Application No. 90301135.1. The hybridised complex is conveniently excited with ultra violet light, preferably at 495 nm wavelength when fluorescein is the chosen fluorophore or preferably at 554 nm when rhodamine is the chosen fluorophore. Whilst we do not wish to be bound by theoretical considerations it is believed that the solution phase embodiments outlined above are not suitable for use with the single stranded products of linear amplification.

The method of the present invention is applicable to all areas of diagnostic medicine and other diagnostic sciences, for example forensic, agricultural, veterinary, food sciences or molecular biology research where it is necessary to detect or measure specific nucleic acid sequences. In particular it is applicable to the detection of infectious micro-organisms and to the detection of point mutations, gene deletions and rearrangements which give rise to various inherited diseases, such as for example cystic fibrosis, alpha-1-antitrypsin deficiency and predisposition to disease.

In this regard the method of the present invention may advantageously be employed in conjunction with the allele specific amplification method referred to as the Amplification Refractory Mutation System (ARMS) which is described and claimed in our European Patent Application No. 89302331.7, Publication No. 0332435 and additionally described by Newton et al in Nucleic Acids Research 17 (7) 2503–2516 (1989). The method as described in Nucleic Acids Research may also be effected by linear amplification or by other amplification techniques as opposed to the polymerase chain reaction as described and claimed in our above-mentioned European Patent Application. ARMS uses primers that allow amplification in an allele specific manner. Allele specificity is provided by the complementarity of the 3'-terminal base of a primer with its' respective allele. Amplification is inhibited when the 3' terminal base of the primer is mismatched. Where specificity of a given primer is not absolute, this can be achieved by destabilising its 3'-terminus by including an additional mismatched base. Both ARMS and PCR can be performed on small ammounts of crude DNA from biological samples and therefore have considerable diagnostic utility.

Allele specific amplification as outlined above may conveniently be effected using a single solid phase for a reaction to detect the presence of both normal and variant alleles of a genetic locus. For a given locus, for example the S locus of the alpha-1-antitrypsin gene (AAT-S locus), the internal control signal primers are labelled with a fluorophore such as fluorescein and both ARMS signal primers are labelled with a different fluorophore such as rhodamine. The different colours green (fluorescein), red (rhodamine) and their combination yellow (red+green) allow the detection of all normal and variant heterozygotes and homozygotes. By way of example two solid phases bind respectively an internal control capture oligonucleotide plus a capture oligonucleotide for the variant sequence of AAT-S locus as well as a further internal control capture oligonucleotide and a capture oligonucleotide for the normal sequence of the AAT-S locus. Subsequent hybridisation with the ARMS amplification products having non-amplifiable tails allows different coloured fluorescent products to be identified. Thus for example a normal individual would show up on the first solid phase as green (fluorescein only), similarly a homozygous S variant individual would show up as green on the second solid phase. A heterozygote would appear yellow on both solid phases (green+red). Similarly a normal individual would show up yellow on the second solid phase and a homozygous S would show up yellow on the first solid phase. The above mentioned aspects are particularly useful in respect of dipstick type assay formats. Also a reduction in the number of solid phases required simplifies the chosen assay.

Allele specific amplification as outlined above may alternatively be carried out in the solution phase. Thus for example each unincorporated non-amplifiable tail primer is removed as hereinbefore described. The reaction mixture is then contacted with a plurality of detection primers under hybridising conditions with each detection primer being conjugated to a different fluorophore. Any convenient fluorophore such as fluorescein, rhodamine, Texas red or lucifer yellow may be used. The presence of each amplification reaction product is then detected for example using fluorescence polarisation as hereinbefore described.

According to a still further feature of the present invention there is provided a kit for the amplification of a target nucleotide sequence which comprises:

a first primer and a corresponding amplification primer for each target nucleotide sequence to be amplified, each first primer comprising:
1) a target binding nucleotide moiety which is substantially complementary to the desired portion of the target nucleotide sequence; and
2) a polynucleotide tail;

the presence of the first primer in the first primer extension product being effective to inhibit formation of a sequence complementary to the polynucleotide tail in the amplification primer extension product.

If desired the first primer may additionally include a nucleotide polymerisation blocking moiety, the said moiety being positioned between the target binding nucleotide moiety and the polynucleotide tail.

If desired the amplification primer may also comprise:
1) a target binding nucleotide moiety which is substantially complementary to the desired portion of the target nucleotide sequence; and
2) a polynucleotide tail;
the presence of the amplification primer in the amplification primer extension product being effective to inhibit formation of a sequence complementary to the polynucleotide tail in a first primer extension product.

If desired the amplification primer may additionally include a nucleotide polymerisation blocking moiety, the said moiety being positioned between the target binding nucleotide moiety and the polynucleotide tail.

The kit of the present invention may, if desired include internal control primers, where appropriate.

The kit of the present invention may, if desired, include appropriate different nucleotides and/or an agent for polymerisation of the nucleotides.

Furthermore, the kit of the present invention may, if desired include solid phase, for binding directly or indirectly to the polynucleotide tails of the primers for example in respect of each target nucleotide sequence to be amplified.

Thus for example, the solid phase may carry a nucleotide sequence substantially complementary to the polynucleotide tail of the primer. If more than one target nucleotide sequence is to be amplified in the same reaction vessel, then the solid phase for binding directly or indirectly to the polynucleotide tail of the primer is preferably distinguishable in respect of each target nucleotide sequence to be amplified.

The expression "target nucleotide sequence" as used herein means a nucleotide sequence comprising the sequence to be amplified. Thus for example if the present invention is applied to the diagnosis of β-thalassaemias a sample may contain as many as 60, for example 50, separate potential variant sequences and therefore the sample would contain as many as 60 target nucleotide sequences all of which may, if desired, be amplified (for example as discussed in European Patent Publication No. 237,362) and the amplified products distinguished according to the present invention.

The term "nucleotide" as used herein can refer to nucleotides present in either DNA or RNA and thus includes nucleotides which incorporate adenine, cytosine, guanine, thymine and uracil as base, the sugar moiety being deoxyribose or ribose. It will be appreciated however that other modified bases capable of base pairing with one of the conventional bases, adenine, cytosine, guanine, thymine and uracil, may be used in the diagnostic first primer and amplification primer employed in the present invention. Such modified bases include for example 8-azaguanine and hypoxanthine. If desired the nucleotides may carry a label or marker so that on incorporation into a primer extension product, they augment the signal associated with the primer extension product, for example for capture on to solid phase.

It will be appreciated that where the process of the present invention is to be used to amplify a target nucleotide sequence which does not contain all four different nucleotides, then an extension product of the first primer and if desired, an extension product of the amplification primer may be formed in the presence of only the appropriate corresponding nucleoside triphosphates and all four different nucleoside triphosphates would not be necessary and the expression "appropriate nucleotides" as used herein is to be understood accordingly.

The agent for polymerisation of the nucleotides may be any compound or system which will function to accomplish the synthesis of primer extension products, including enzymes. Suitable enzymes for this purpose include, for example, *E. coli* DNA Polymerase I, Klenow fragment of *E. coli* DNA polymerase I, T4 DNA polymerase, other available DNA polymerases, reverse transcriptase, and other enzymes, including thermostable enzymes. The term "thermostable enzyme" as used herein refers to any enzyme which is stable to heat and is heat resistant and catalyses (facilitates) combination of the nucleotides in the proper manner to form the primer extension products which are complementary to each nucleic acid strand. Generally, the synthesis will be initiated at the 3' end of each primer and will proceed in the 5' direction along the template strand, until synthesis terminates, producing molecules of different lengths. There may be enzymes for example, thermostable enzymes, however, which inititate synthesis at the 5' end and proceed in the other direction, using the same process as described above. A preferred thermostable enzyme which may be employed in the process of the present invention is that which can be extracted and purified from *Thermus aquaticus*. Such an enzyme has a molecular weight of about 86,000–90,000 daltons as described in European Patent Publication No. 237,362 (see also European Patent Publication No 258,017). *Thermus aquaticus* strain YT1 is available without restriction from the American Type Culture Collection, 12301 Parklawn Drive, Rockville, Md., U.S.A. as ATCC 25,104.

The term "primer" is used herein to refer to a binding element which comprises an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, ie., in the presence of appropriate nucleotides and an agent for polymerisation such as a DNA polymerase in an appropriate buffer ("buffer" includes pH, ionic strength, cofactors, etc.) and at a suitable temperature. In respect of the first primer the oligonucleotide portion of the binding element is termed the "target binding nucleotide moiety".

The term "oligonucleotide" as used herein is defined as a molecule comprised of two or more deoxyribonucleotides or ribonucleotides, preferably more than three. Its exact size will depend on many factors, such as the reaction temperature, salt concentration, the presence of denaturants such as formamide, and the degree of complementarity with the sequence to which the oligonucleotide is intended to hybridise.

The primer is preferably single stranded for maximum efficiency in amplification, but may alternatively be double standed. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer and use of the method. For example, depending on the complexity of the target sequence, the first and amplification primers typically contain 12–35, for example, 15–35 nucleotides capable of hybridisation to the target nucleotide sequence, although they may contain more or fewer such nucleotides. Primers having only short sequences capable of hybridisation to the target nucleotide sequence generally require lower temperatures to form sufficiently stable hybrid complexes with the template.

The term "complementary to" is used herein in relation to nucleotides to mean a nucleotide which will base pair with another specific nucleotide. Thus adenosine triphosphate is complementary to uridine triphosphate or thymidine triphosphate and guanosine triphosphate is complementary to cytidine triphosphate. It is appreciated that whilst thymidine triphosphate and guanosine triphosphate may base pair under certain circumstances they are not regarded as complementary for the purposes of this specification. It will also be appreciated that whilst cytosine triphosphate and adenosine triphosphate may base pair under certain circumstances they are not regarded as complementary for the purposes of this specification. The same applies to cytosine triphosphate and uracil triphosphate.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. Commonly, however, the primers have exact complementarity except with respect to analyses effected according to the method described in Nucleic Acids Research 17 (7) 2503–2516 (1989) or a corresponding method employing linear amplification or an amplification technique other than the polymerase chain reaction.

The first primer and if desired the amplification primer comprise a target binding nucleotide moiety (as hereinbefore defined), a polynucleotide tail and, if desired, a polymerisation blocking moiety. The polynucleotide tail can be any chosen sequence, provided 1) that it is long enough to provide a stable hybrid with a substantially complementary sequence under given stringency conditions, and 2) that it be sufficiently different from the target binding nucleotide moiety, to avoid significant hybrid formation between
   a) the target nucleotide sequence and the polynucleotide tail; and
   b) the polynucleotide tail and the target binding nucleotide moiety.

This latter condition is required to prevent molecular confusion with concomitant appearance of false results.

The polynucleotide tail may code for a particular gene product or products, or may code for no gene product at all. Thus, any structural gene or portion thereof could be used as the polynucleotide tail. A preferred sequence, however, would not code for a given gene since such coding may cross hybridise with complementary gene sequences present in the analyte. It is thus preferred to choose a polynucleotide sequence which is non-coding, and not likely to be complementary to sequences in the analyte such as, for example, sequences comprising poly deoxy G, poly deoxy A, poly deoxy GA, poly deoxy GAT, poly deoxy GTA, or any other low complexity (repeating) sequence or any randomly generated sequence. Any such (randomly generated) sequence may be checked against an appropriate nucleotide sequence database to ensure that binding will not be expected to take place between the randomly generated sequence and the target sequence. The randomly generated sequence may be further checked to ensure that no spurious binding takes place with the target or other sequences in the analyte by dot blot analysis of samples of the analyte using methods known per se.

The term "polynucleotide" as used herein means a sequence of more than one nucleotide (as hereinbefore defined) and thus includes the term "oligonucleotide" (as hereinbefore defined).

The term "polymerisation blocking moiety" as used herein means any moiety which when linked for example covalently linked, between a first nucleotide sequence(s) and a second nucleotide sequence(s) is effective to inhibit and preferably prevent, more preferably completely prevent amplification (which term includes any detectable copying beyond the polymerisation blocking moiety) of either the first or the second nucleotide sequence(s) but not both such first and second sequences. In general an agent for polymerisation will initiate polynucleotide synthesis at the 3' end of a primer and will proceed in the 5' direction along the template strand and thus in general the polynucleotide tail will be 5' of the polymerisation blocking moiety and the target binding nucleotide moiety will be 3' of the polymerisation blocking moiety. Where however an agent for polymerisation is to be used which initiates synthesis at the 5' end of a primer and proceeds in the 3' direction along the template strand, then the target binding nucleotide moiety will be 5' of the polymerisation blocking moiety and the polynucleotide tail will be 3' of the polymerisation blocking moiety. Preferably the polymerisation blocking moiety comprises a moiety inert under the conditions of the method of the invention.

If desired the target binding nucleotide moiety may carry more than one polynucleotide tail and/or the polynucleotide tail(s) may carry more than one target binding nucleotide moiety. In such circumstances the presence of a polymerisation blocking moiety between the polynucleotide tail(s) and the target binding nucleotide moiety (moieties) may be unnecessary as for example disclosed in European Patent application No. 317077. Similarly the target binding nucleotide moiety and the polynucleotide tail may be linked to one another, the moiety and tail however being disposed in the opposite sense to one another. In such a situation, again, the presence of a polymerisation blocking moiety between the polynucleotide tail and the target binding nucleotide moiety may not be necessary. In such a situation the target binding moiety would generally be disposed in the 5'—→3' sense and the polynucleotide tail generally disposed in the 3'—→5' sense, with linkage via their 5' termini.

Preferably a polymerisation blocking moiety, where present, comprises a moiety inert under the conditions of the method of the invention employed and linked, for example covalently linked, between the polynucleotide tail and the target binding nucleotide moiety. A wide range of such moieties may be envisaged for this purpose as exemplified below. For example the polymerisation blocking moiety may comprise a bead, for example a polystyrene, glass or polyacrylamide bead or the polymerisation blocking moiety may comprise a transition metal such as for example iron, chromium, cobalt or nickel (for example in the form of a transition metal complex with the polynucleotide tail and the target binding nucleotide moiety) or an element capable of substituting phosphorus such as for example arsenic, antimony or bismuth linked between the polynucleotide tail and the target binding nucleotide moiety. The blocking moiety might similarly but less preferably involve substitution of the usual phosphate linking groups f or example where oxygen is replaced leading to inter alia phosphorodithioates, phosphorothioates, methylphosphonates, phosphoramidates such as phosphormorpholidates, or other residues known per se. Alternative blocking moieties include any 3'-deoxynucleotide not recognised by restriction endonucleases and seco nucleotides which have no 2'-3' bond in the sugar ring and are also not recognised by restriction endonucleases.

The minimum molecular length between the said tail and the target binding nucleotide moiety is generally one atom. The said molecular length is conveniently the equivalent of from 1 to 200 nucleotides, advantageously the equivalent of from 1 to 10 nucleotides, preferably the equivalent of 2-4 nucleotides, for example the equivalent of about 2 or about 4 nucleotides, depending on the nature of the moiety or combination of different moieties.

Thus for example the polymerisation blocking moiety may comprise at least one deoxy ribofuranosyl naphthalene or ribofuranosyl naphthalene moiety, advantageously at least 2 (such as 2 to 10), preferably at least 3 (such as 3 to 8), more preferably at least 4 (such as 4 to 6) such moieties. If desired the deoxyribofuranosyl or ribofuranosyl naphthalene moiety may be linked to the adjacent nucleotides via a 3'-furanosyl linkage or preferably via a 2'-furanosyl linkage. In particular deoxyribofuranosyl naphthalene moieties may be used, linkage to the adjacent nucleotides of the polynucleotide tail and the target binding nucleotide moiety being via a 2'-deoxyribofuranosyl group or more preferably a 3'-deoxyribofuranosyl group. If desired the polymerisation blocking moiety may comprise a straight chain alkylene grouping having one or more carbon atoms, for example at least 2 conveniently at least 3, advantageously at least 4, preferably at least 5, more preferably at least 6 carbon atoms. The upper limit on the number of carbon atoms in the alkylene chain is only determined by synthetic convenience. Thus for example the grouping may contain from 6 to 20 carbon atoms, which alkylene grouping may if desired carry at least one, for example 1–6 $C_{1-3}$ alkyl substituents. The alkylene grouping, or the backbone thereof where substitution is present, conveniently has at least 7, 8, 9, 10, 11 or 12 carbon atoms (the order of preference being 7<8<9<10<11<12) as the minimum number and 19, 18, 17 and 16 carbon atoms (the order of preference being 19<18<17<16) as the maximum number of carbon atoms.

The term "amplification primer" is used herein to refer to a primer which is capable of hybridising to the nucleic acid strand which is complementary to the nucleic acid strand to which the first primer is capable of hydridising, the "amplification primer" having a nucleotide sequence such that it is capable of hybridising to a first primer extension product, after separation from its complement, whereby the first primer extension product serves as a template for synthesis of an extension product of the amplification primer, thereby facilitating amplification.

Figure 1:
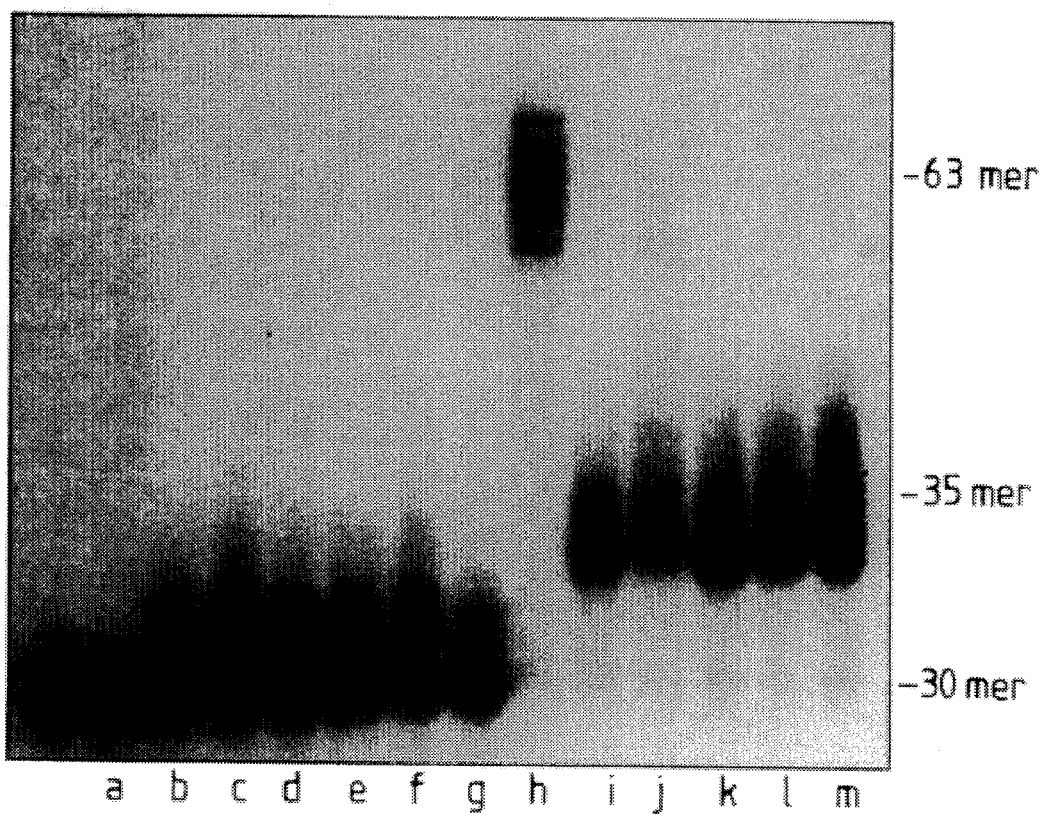
FIG. 1 is a representation of an autoradiograph showing the results of using deoxyribofuranosyl, alkylene and methyl phosphonate polymerisation blocking moieties in primers employed in the method of the present invention.

The invention is illustrated, but not limited, by the following Examples in which the oligonucleotides (5'-3') are as stated below:

Oligonucleotide design

The nucleotide primary structures of the non-amplifiable tails were generated using a computer program to generate random nucleotide sequences. The nucleotide sequences of candidate non-amplifiable tails were inspected for guanosine content; particularly G-rich sequences or sequences with more than three consecutive G residues were discarded. The remaining candidates were tested against the primate DNA nucleotide sequences in Genbank version 63.0 (Nucleic Acids Research, 12, 387–395, 1984) allowing 2 mismatches. Candidates that matched were also discarded. All oligonucleotides were synthesised using an Applied Biosystems 380A or 380B DNA synthesiser according to the manufacturer's protocols:

Oligonucleotide 1

AATTCCGTGCATAAGGCTGTGCTGAC-
CATCGACGAGAAAGGGACTGAAGCTGCTGGGGCCATG

Oligonucleotide 2

AATTCCGTGCATAAGGCTGTGCT-
GNNNNTCGACGAGAAAGGGACTGAAGCT-
GCTGGGGCCATG (wherein N represents a 2'-deoxyribofuranosyl naphthalene moiety, the 5' and 3' terminal naphthalene moieties being linked via the 3'-PO$_4$ grouping to the adjacent nucleotide).

Oligonucleotide 3

AATTCCGTGCATAAGGCTGTGCTGNNTC-
GACGAGAAAGGGACTGAAGCTGCTGGGGCCATG (wherein N represents a 3'-deoxyribofuranosyl naphthalene moiety, the naphthalene moieties being linked via the 2'-PO$_4$ grouping to the adjacent nucleotide thereby introducing a kink into the DNA chain).

Oligonucleotide 4

AATTCCGTGCATAAGGCTGTGCT-
GNNNNTCGACGAGAAAGGGACTGAAGCT-
GCTGGGGCCATG (wherein N represents a 3'-deoxyribofuranoysl naphthalene moiety, the naphthalene moieties being linked via the 2'-PO$_4$ grouping to the adjacent nucleotide thereby introducing a kink into the DNA chain).

Oligonucleotide 5

CATGGCCCCAGCAGCTTCAGTCCCTTTCTC

Oligonucleotide 5 is a 30-mer which is complementary to the 3' end of all the oligonucleotides 1–4 described above and oligonucleotides 6 and 8 below; the purpose of the experiment being to see whether oligonucleotide 5 can be extended using the above-described oligonucleotides 1–4 and the below described oligonucleotides 6 and 8 as template.

Oligonucleotide 6

AATTCCGTGCATAAGGCTGTGCT-
GNNNNTCGACGAGAAAGGGACTGAAGCT-
GCTGGGGCCATG (wherein NNNN represents a straight chain alkylene moiety of 16 carbon atoms).

Oligonucleotide 7

TTTTTTTTTTTATCAACTTACTTGCCTATA this oligonucleotide may be used for attachment to a solid phase via an amino link on the 5' end of the final T of the poly T region. The sequence of nucleotides 3' of the poly T region is complementary to the polynucleotide tail of an ARMS primer specific f or the normal S locus of the alpha-1-antitrypsin gene.

Oligonucleotide 8

AATTCCGTGCATAAGGCTGTGCT-
GNNNNTCGACGAGAAAGGGACTGAAGCT-
GCTGGGGCCATG in which N represents a 4-methyl phosphonate substituted thymidine residue.

Similarly oligonucleotides 6 and 8 are used as template to see whether oligonucleotide 5 can be extended.

EXAMPLE 1

The above-mentioned oligonucleotides were used to demonstrate the failure of Taq DNA polymerase to extend an oligonucleotide primer across a nucleotide polymerisation blocking moiety present in a template DNA strand.

Oligonucleotide 5 (30 p moles) was labelled at the 5' terminal hydroxyl group using γ $^{32}$P-ATP 75 µCi (15 pmoles) (Amersham) and T4 polynucleotide kinase (4 units) in a 50 µl reaction volume containing 50 mM Tris.HCl pH7.6, 10 mM MgCl$_2$, 5 mM DTT 100 µM spermidine and 100 µM EDTA. The kinase reaction was carried out at 37° C. for 20 minutes. To completely destroy any remaining kinase activity the reaction mixture was boiled for 5 minutes, followed by a phenol:chloroform (1:1) extraction (37.5 µl of each component). This was followed by mixing and centrifugation of the mixture for 2 minutes at 13,500 r.p.m. The aqueous layer was removed and kept for the reactions.

Oligonucleotides 1–4, 6, and 8 were purified by acrylamide gel electrophoresis, u.v. shadowing, butan-1-ol concentration, phenol/chloroform extraction and ethanol precipitation. Oligonucleotide 5 was purified by HPLC using an anion exchange column (Mono Q, Pharmacia) equilibrated with Buffer A (10 mM NaOH, 0.5M NaCl). The oligonucleotide was eluted with a gradient of Buffer B (10 mM NaOH, 0.9M NaCl) 0–100% in 60 minutes. Fractions corresponding to the product peak were pooled and desalted using a PD10 column (Pharmacia) then concentrated by drying under vacuum. The purity of the oligonucleotides was checked by 5' $^{32}$P labelling using 5' $^{32}$P ATP (Amersham) and T4 polynucleotide kinase followed by polyacrylamide gel electrophoresis under denaturing (7M urea) conditions.

The following reactions were effected:

|   |   |   | Length of product expected if bridge stops enzyme |   |
|---|---|---|---|---|
| a) | Labelled 5 | + dNTPs (ACGT) | 30 | No extension as no template |
| b) | Labelled 5 | + 1 | " | |
| c) | Labelled 5 | + 2 | " | |
| d) | Labelled 5 | + 3 | " | No dNTPs |
| e) | Labelled 5 | + 4 | " | |
| f) | Labelled 5 | + 6 | " | |
| g) | Labelled 5 | + 8 | " | |
| h) | Labelled 5 | + 1 + dNTPs (ACGT) | 63 | Control |
| i) | Labelled 5 | + 2 + dNTPs (ACGT) | 35 | |
| j) | Labelled 5 | + 3 + dNTPs (ACGT) | 35 | |
| k) | Labelled 5 | + 4 + dNTPs (ACGT) | 35 | |
| l) | Labelled 5 | + 6 + dNTPs (ACGT) | 35 | |
| m) | Labelled 5 | + 8 + dNTPs (ACGT) | 35 | |

If DNA polymerisation is not prevented by the polymerisation blocking moiety the full length oligonucleotide will be copied to give a 63 mer product as expected in control reaction (h). However, if the blocking moiety stops the enzyme (Taq DNA polymerase) then a 35 mer product is expected, this representing chain extension up to the start of the polymerisation blocking moiety.

Each reaction contained 1 pmole of labelled oligonucleotide 5 and 3 pmoles of the appropriate long oligonucleotide 1–4, 6 and 8. The dNTPs, where required as shown, were added to a final concentration of 100 μM each. There was no denaturation step before 2 units of Taq DNA polymerase (Cetus-Amplitaq) were added to make a final reaction volume of 100 μl containing 1.2 mM magnesium chloride, 50 mM potassium chloride, 10 mM Tris HCl (pH 8.3) and 0.01% gelatin (1×buffer A). The tubes were placed in a 91° C. water bath for 2 minutes then at 60° C. for 58 minutes. A 5 μl aliquot was taken from each tube. In addition 1 μl of labelled oligonucleotide 5 was added to 89 μl autoclaved deionised water (Milli Q Standard) and 10 μl of 10× buffer A (1×buffer A being as herein defined) and 5 μl of this taken to act as a marker for oligonucleotide 5. All the 5 μl aliquots were mixed with 5 μl formamide dye (80% formamide, 10 mM NaOH 1 mM EDTA and 0.1% Bromophenol Blue) and denatured by boiling for 5 minutes. The aliquots were electrophoresed on a pre-run (1 hr, 500 V) 15% denaturing polyacrylamide gel, 8M Urea in 1×TBE buffer (0.089M TrisBorate, 0.089M boric acid, 0.002M EDTA) for 5 hours at 900 V and autoradiographed for two hours at room temperature with X-ray film.

The results obtained are shown in the autoradiograph depicted in FIG. 1. These demonstrate that the polymerisation blocking moieties present in oligonucleotides 2, 3, 4, 6 and 8 stop Taq DNA polymerase catalysed oligonucleotide extension.

Preparation of Starting Materials

A) Preparation of 2'-deoxynaphthalene oligonucleotide (2)

1) Preparation of oligodeoxyribonucleotide

The fully protected oligodeoxyribonucleotide of sequence (2) was prepared on an Applied Biosystems 380A DNA synthesiser from 5'-α,α-bis(p-methoxyphenyl)benzyl-$N^2$-isobutyryl-2'-deoxyguanosine bound to controlled pore glass via 3'-OH and a succinylglycylglycylaminopropyl spacer (Applied Biosystems Inc) and the 2-cyanoethyl-N,N-diisopropylaminophosphoramidite of 5'-α,α-bis(p-methoxyphenyl)benzyl-$N^6$-benzoyl-2'-deoxyadenosine, 5'-α,α-bis(p-methoxyphenyl)benzyl-$N^4$-benzoyl-2'-deoxycytidine, 5'-α,α-bis(p-methoxyphenyl)benzyl-$N^2$-isobutyryl-2'-deoxyguanosine, 5'-α,α-bis(p-methoxyphenyl)benzyl-2'-deoxythymidine (Applied Biosystems Inc) and 1-[2'-deoxy-β-D-ribofuranosyl-5'-O-α,α-bis(p-methoxyphenyl)benzyl-3'-(methoxymorpholinophosphine)]naphthalene (prepared as described in (2) below). Alternatively, the fully protected oligodeoxyribonucleotide sequence and those referred to below may be prepared by the manual methods as described by Atkinson and Smith in 'Oligonucleotide Synthesis, a Practical Approach' (M. J. Gait Editor, IRL Press, Oxford, Washington D.C., pages 35–81).

1-[2'-deoxy-β-D-ribofuranosyl-5'-O-α,α-bis(p-methoxyphenyl)benzyl- 3'-(methoxy-N-morpholinophosphine)]naphthalene (70 mg) in anhydrous acetonitrile (1 ml) was used in place of a normal phosphoramidite at position 5 on a Applied Biosystems 380A DNA synthesiser to introduce the naphthalene substituted residues into the oligonucleotide where indicated by "N" in oligonucleotide 2 above. The procedures consisted briefly of: (1) removal of the α,α-bis(p-methoxyphenyl)benzyl group with 3% trichloroacetic acid in dichloromethane; (2) Coupling of 1-[2'-deoxy-β-D-ribofuranosyl-5'-O-α,α-bis(p-methoxyphenyl)benzyl-3'-(methoxy-N-morpholino-phosphine)]naphthalene (0.1M solution) activated by tetrazole for 3 minutes; (3) iodine oxidation of the intermediate phosphite to a phosphate; (4) a capping step with acetic anhydride. The detritylated oligodeoxyribonucleotide sequence was cleaved from the solid support and completely deprotected by treatment with ammonium hydroxide solution (sp.g. 0.88) for 16 h. at 55° C. The ammonium hydroxide solution was evaporated and the residue dissolved in water (1 ml). An aliquot of the solution containing the oligodeoxyribonucleotide was purified as follows:

An aliquot of the crude oligodeoxyribonucleotide (225 μl) was precipitated by the addition of 25 μl of 3M sodium acetate (pH 5.2), mixing and addition of 750 μl of absolute ethanol to the mixture. After further mixing the mixture was left at ambient temperature (25° C.) for one hour and then at 4° C. for a further one hour in order to encourage precipitation of the DNA. The mixtures were centrifuged for 10 minutes at 13,500 r.p.m and the supernatant removed. The pellets were left to air dry for an hour and then reconstituted with 50 μl of formamide dye (80% formamide, 10 mM NaOH, 1 mM EDTA 0.1% bromophenol blue) at 37° C. for 20 minutes. The sample was boiled for 5 minutes, immediately put on ice and loaded onto a 15% polyacrylamide denaturing gel (7M Urea) in 100 mM TrisBorate, 2 mM EDTA, pH 8.3 buffer. The gel had been prerun for 1 hour at 500 V. The samples were electrophoresed overnight at 50 V, that being until the bromophenol dye had run to the bottom of the (0.3×25×17 cm³) gel. The oligodeoxyribonucleotide was visualised by ultraviolet shadowing at 254 nM on Merck 5554 20×20 aluminium backed thin layer chromotography plates covered with Saran wrap. The product bands were excised using a new scalpel for each oligodeoxyribonucleotide to prevent contamination. The gel slices were placed into 1 inch lengths of treated 1 inch wide dialysis tubing containing 1 ml 10 mM TrisBorate, 0.2 mM EDTA, pH 8.3. Treatment of the tubing consisted of boiling in 1 mM EDTA for 10 minutes and rinsing three times by boiling in autoclaved deionised water (Milli Q). The oligodeoxyribonucleotide was eluted from the gel slices by electroelution at 200 V for one and a half hours at the end of which the polarity was reversed for about 45 seconds to remove any DNA stuck to the tubing. The electroeluate was transferred into a quartz spectrophotometer cuvette and the optical density read against the elution buffer. The concentration of the oligodeoxyribonucleotide was calculated from the optical density of the solution. The oligodeoxyribonucleotide was then concentrated by butanol extraction until the volume of the aqueous layer was about 500 μl. A phenol chloroform 1:1 mixture (500 μl) was then added, mixed and the mixture centrifuged at 13,500 r.p.m for 2 minutes. The aqueous phase was removed and concentrated further by butanol extraction to about 50 μl. This was then dried under vacuum then reconstituted to 1 pmole/μl with autoclaved deionised water (Milli Q).

The purity of the oligodeoxyribonucleotide was checked by labelling 1 pmole of the purifed deoxynucleotide at the 5' terminal hydroxyl group using $\gamma^{32}$P ATP 10 μCi (2 pmoles) (Amersham) and $T_4$ polynucleotide kinase (4 units) in a 20 μl reaction volume containing 50 mM Tris HCl pH7.6, 10 mM $MgCl_2$, 5 mM DTT, 100 μM spermidine and 100 μM EDTA. The kinase reaction was carried out at 37° C. for 20 minutes. Then 2 μl of the reaction mix were added to 5 μl of the formamide dye, boiled for 5 minutes put immediately on ice and run on a 15% denaturing polyacrylamide gel (7M Urea) prerun for 1 hour at 500 V and electrophoresed for 3 hours at 800 V. The gel was exposed to X-ray film for 30 minutes and the resulting autoradiograph showed that the gel purifed oligodeoxynucleotide was of the required high purity.

2) Preparation of 1-[2'-Deoxy-β-D-ribofuranosyl-5'-O-α,α-bis(p-methoxyphenyl)benzyl-3'-(methoxy-N-morpholinophosphine)]naphthalene 1-[2'-Deoxy-β-D-ribofuranosyl-5'-O-α,α-bis(p-methoxyphenyl)benzyl]naphthalene (0.87 g, 1.6 mmole) [prepared as described in 2a below] was stirred with chloromethoxy)-N-morpholinophosphine (0.3 g, 1.6 mmole) and N,N' diisopropylethylamine (0.85 g, 6.6 mmole) in $CH_2Cl_2$ (30 ml) at −40° C. under $N_2$. The crude product was obtained after 10 min at ambient temperature by removal of the solvent under reduced pressure. The product 1-[β-D-2'-deoxyribofuranosyl-5'-O-α,α-bis(p-methoxyphenyl)benzyl- 3'-(methoxy-N-morpholinophosphine)]naphthalene (0.8 g, 73%) was isolated as a white solid by flash chromatography on silica gel (Merck Art 9385) with eluant of $EtOAc:Et_3N$ (66:1).

M/S $(M+H)^+694$ δ ($CDCl_3$, 200 MHz); 7.83 (3H,m,ArH), 7.33 (13H,m,ArH), 6.82(4H,m,ArH), 5.88 (1H,dd,H-1'), 4.65 and 4.48 (1H,m,H-3'), 4.3 and 4.15 (1H,m,H-4'), 3.8 (7H,m,$OCH_3$ and H-5') 3.6 and 3.52 (4H,2xt morpholino protons), 3.46 and 3.39 (3H, 2xd,$POCH_3$), 3.12 and 3.03 (4H,m,Morpholino protons), 2.57 (1H,m,H-2'), 2.18 (1H,m, H-2').

a) Preparation of 1-[2'-Deoxy-β-D-ribofuranosyl-5'-O-α, α-bis(p-methoxyphenyl)benzyl]naphthalene.

1-(2'-Deoxy-β-D-ribofuranosyl)naphthalene [(0.88 g, 4 mmole) prepared as described in 2b below] was dried by co-evaporations with anhydrous pyridine (2×10 ml) and then stirred at ambient temperature for 2 h with α,α-bis(p-methoxyphenyl)benzyl chloride (1.3 g, 4.3 mmole) in anhydrous pyridine (10 ml). Methanol (5 ml) was added and the residual oil remaining after the solvent was removed in vacuo taken up in chloroform (50 ml). The crude product was obtained by successively washing the organic solution with equal volumes of a saturated solution of sodium hydrogen carbonate (2×) and with water (2×) and then removal of the solvent under reduced pressure after drying over magnesium sulphate ($MgSO_4$). The product 1-[2'-deoxy-β-D-ribofuranosyl-5'-O-α,α-bis(p-methoxyphenyl)benzyl]naphthalene (0.6 g; 30.5%) was isolated as a pale brown solid by chromatography on silica gel (Merck Art 9385) with elution by pyridine:methanol:dichloromethane (1:3:196), follwed by co-evaporation with toluene.

δ ($CDCl_3$, 200 MHz); 8.03 to 6.82, (20H,m, ArH), 5.88 (1H, m, H-1'), 4.47 (1H, m, H-3'), 4.12 (1H, m, H-4'), 3.78 (7H, m, 2×$CH_3$ and H-5'), 3.43 (1H, m, H-5'), 2.50 (1H, m, H-2'), 2.12 (1H, m, H-2').

b) Preparation of 1-(2'-Deoxy-β-D-ribofuranosyl)naphthalene

1-[2'-deoxy-β-D-ribofuranosyl-3',5'-(1,1,3,3 tetraisopropyldisiloxyl)]naphthalene [(0.12 g, 0.24 m mole) prepared as described in 2c below] in a mixture of pyridine (10%); water (10%) and tetrahydrofuran (80%), (2 ml) was added to a solution of n-tetrabutylammonium fluoride (0.73 m mole) in THF and allowed to stand at ambient temperature for 16 hours. The product, 1-(2'-deoxy-β-D-ribofuranosyl)naphthalene (19 mg, 35%) was isolated as a white solid after removal of the solvent in vacuo and purification by chromatography on silica gel (Merck Art 9385) with elution by methanol:dichloromethane (1:9).

δ ($CD_3OD$, 200 MHz); 8.05(1H,m,ArH), 7.80(3H,m,ArH) 7.48(3H,m,ArH), 5.87(1H,dd,H-1'), 4.35(1H,ddd,H-3'), 4.05 (1H,ddd,H-4'), 3.75(2H,dd,2H-5'), 2.48(1H,ddd,H-2'), 1.99 (1H,ddd,H-2')

c) Preparation of 1-[2'-Deoxy-β-D-ribofuranosyl-3',5'-(1, 1,3,3-tetraisopropyldisiloxyl)]naphthalene.

1-[β-D-Ribofuranosyl-2'-phenylthioformate-3',5'-(1,1,3, 3-tetraisopropyldisiloxyl)]naphthalene, [(0.4 g, 0.6 mmole) prepared as described in 2d below] and 2,2'-azobis(2-methylpropionitrile), (0.1 g, 0.6 mmole) and n-tributyltin hydride (2.8 g, 2.7 mmole) were refluxed in toluene (20 ml) for 30 minutes. The product, 1-[β-D-2'-deoxyribofuranosyl-3'-5'-(1,1,3,3-tetraisopropyldisiloxyl)]naphthalene (0.12 g, 51%) was isolated by removal of the solvent under reduced pressure and purification on silica gel (Merck Art 9385) with elution by petrol (b.p.40/60):dichloromethane (1:1.5). M/S M (486).

d) Preparation of 1-[β-D-Ribofuranosyl-2'-phenylthioformate- 3',5'(1,1,3,3-tetraisopropyldisiloxyl)]naphthalene 1-[β-D-Ribofuranosyl-3',5'-(1,1,3,3-tetraisopropyldisiloxyl)]naphthalene [(0.4 g, 0.8 mmole) prepared as described in 2e below] in dry acetonitrite (25 ml) was stirred for 24 hours at ambient temperature with 4-dimethylaminopyridine (0.6 g, 4.8 mmole) and phenylthiochloroformate (0.7 g, 4.0 mmole). Ethyl acetate (200 ml) was added and the solution sequentially washed with equal volumes of a saturated solution of sodium hydrogen carbonate and with water. The crude product was obtained after drying the solution over magnesium sulphate and removing the solvent under reduced pressure. The product 1-[β-D-ribofuranosyl-2'-phenylthioformate-3',5'-(1,1,3,3-tetraisopropyldisiloxyl)]naphthalene (0.45 g, 88%) was isolated as a white solid by flash chromatography on silica gel (Merck Art 9385) with elution by ethyl acetate:petrol (b.p.40/60) (1:12.3). M/S $(M+NH_4)^+$ 656, $(M+H)^+$639.

e) Preparation of 1-[β-D-Ribofuranosyl-3'-5'-(1,1,3,3-tetraisopropyldisiloxyl)]naphthalene 1-(β-D-Ribofuranosyl)naphthalene [(1.0 g, 3.8 mmole) prepared as described by Ohrui, H.; Kuzuhara, H.; Emoto, S. Agr, Biol. Chem. 1972, 36 (9), 1651] in dry pyridine (15 ml) was stirred for 2 hours at room temperature with 1,3-dichloro-1,1,3,3-tetraisopropyldisiloxane (1.6 g, 5 mmole). Dichloromethane (450 ml) was added and the solution washed sequentially with equal volumes of a saturated solution of sodium hydrogen carbonate and saturated brine. The crude product, (2.6 g) was obtained after drying the organic solution over magnesium sulphate and removal of the solvent under reduced pressure. The product, 1-[β-D-Ribofuranosyl-3',5'-(1,1,3,3-tetraisopropyldisiloxyl)]naphthalene (0.8 g, 1.6 mmole, 42%) was isolated as a colourless oil by flash chromatography on silica gel (Merck Art 9385) eluted with dichloromethane.

M/S 520 $(M+NH_4)^+$, 503$(M+H)^+$, δ ($CDCl_3$, 200 MHz); 8.12, 7.82, 7.52, (7H,m,ArH), 5.68 (1H,s,H-1'), 4.38 (1H, dd,H-3'), 4.28 (1H,d,H-5'), 4.18 (1H,d,H-2'), 4.13 (2H,m,H-4' and H-5'), 1.0 (28H,m,4×$\underline{CH}(CH_3)2$)

B) Preparation of 3'-deoxynaphthalene oligonucleotides (3) and (4)

1) Oligonucleotide preparation

The fully protected oligodeoxyribonucleotides of sequence (3) and (4) as hereinbefore defined were prepared as described in Preparation A1 above, except that the position 5 on an Applied Biosystems DNA synthesiser contained a solution of 1-[3'-deoxy-5'-O-α,α-bis(p-methoxyphenyl) benzyl-2'-(methoxy-N,N-diisopropylaminophosphine)-β-D-ribofuranosyl]naphthalene [(7.0 mg) prepared as described in B2 below] in anhydrous $CH_3CN$ (1 ml) and the phosphoramidite was coupled by a standard coupling reaction used for normal phosphoramidites.

The oligodeoxyribonucleotide was cleaved from the solid support, deprotected and purified by the procedure described in Preparation A1 above.

2) Preparation of 1-[3'-deoxy-5'-O-α,α-bis(p-methoxyphenyl)benzyl- 2'-(methoxy-N,N-diisopropylaminophoshine)-β-D-ribofuranosyl]naphthalene.

1-[3'-deoxy-5'-O-α,α-bis(p-methoxyphenyl)benzyl-β-D-ribofuranosyl]naphthalene (0.78, 1.3 mmole) [prepared as described in 2a below] and N,N-diisopropylethylamine (0.67 g, 5.2 mmole) in anhydrous $CH_2Cl_2$ (30 ml) at –40° C. was stirred with chloro-N-diisopropylmethoxyphosphine (0.26 g, 1.3 mmole). The reaction mixture was maintained under an atmosphere of dry $N_2$ and attained ambient temperature after 1 hour. The product, 1-[3'-deoxy-5'-O-α,α-bis(p-methoxyphenyl)benzyl-2'-(methoxy-N,N-diisopropylaminophosphine)-β-D-ribofuranosyl]naphthalene (0.8 g, 87%) was isolated as a yellow solid (mixture of diastereoisomers) by removing the solvent in vacuo followed by flash chromatography on silica gel (Merck Art No. 9385) with elution by $Et_3N:EtOA_c$ (1:66) and by evaporation of the solvent.

δ ($CDCl_3$, 200 MHz); 8.3 and 8.17 (1H,m,naphthalene protons), 7.80 (3H,m,naphthalene protons), 7.53 (3H,m, naphthalene protons), 7.28 (9H,m,ArH), 6.83 (4H,m,ArH), 5.8 and 5.75 (1H,s,H-1'), 4.65 (1H,m,H-4'), 4.5(1H,m,H-2'), 3.78 (6H,s, 2× $OCH_3$), 3.65 (2H,m,2H-5'), 3.45 and 3.36 (3H,d,$POCH_3$), 2.09 and 2.02 (2H,m, 2H-3'), 1.21 (14H,m, $2CH(CH_3)_2$).

a) Preparation of 1-[3'-Deoxy-5'-O-α,α-bis(p-methoxyphenyl)-benzyl-β-D-ribofuranosyl]naphthalene 1-(3'-Deoxy-β-D-ribofuranosyl)naphthalene [(0.44 g, 1.8 mmole) prepared as described in 2b below] in dry pyridine (10 ml) was treated with O-α,α-bis(p-methoxyphenyl)benzyl chloride (0.97 g, 2.9 mmole) for 2 hours at ambient temperature. Excess O-α,α-bis(p-methoxyphenyl)benzyl chloride was destroyed by the addition of MeOH (10 ml) and $CH_2Cl_2$ (50 ml) was added. The crude product was obtained by successively washing the organic solution with $NaHCO_3$ aq (2×50 ml) and with water (2×50 ml) and by evaporation of the solvent in vacuo after drying over $MgSO_4$. 1-[3'-Deoxy-5'-O-α,α-bis(p-methoxyphenyl)benzyl-β-D-ribofuranosyl]naphthalene (0.7 g, 71%) was isolated as a brown foam after flash chromatography on silica gel (Merck, Art 9385) with eluant of $MeOH:CH_2Cl_2$ (1:99) and by removal of the solvent in vacuo followed by co-evaporation with toluene.

δ ($CD_3OD$, 200 MHz); 8.18 (1H,m,naphthalene protons), 7.83 (3H,m,naphthalene protons), 7.5 (3H,m,naphthalene protons), 7.24 and 6.86 (13H,m,ArH), 5.6 (1H,br.s.H-1'), 4.62 (1H,m,H-4'), 4.37 (1H,m,H-2') 3.78(6H,d,$OCH_3$), 3.43 (2H,dd,2H-5'), 2.07 (1H,ddd,H-3'), 1.86 (1H,ddd,H-3').

b) Preparation of 1-(3'-Deoxy-β-D-ribofuranosyl)naphthalene 1-(2',3'-Anhydro-β-D-ribofuranosyl)naphthalene [(2.5 g, 10.3 mmole) prepared as described in 2c below] in dry THF (50 ml) was added gradually to a stirred suspension of $LiAlH_4$ (1.52 g, 40 mmole) in THF (50 ml), then maintained in an atmosphere of $N_2$ for 16 hours at ambient temperature. Excess $LiAlH_4$ was destroyed by the gradual addition of $THF/H_2O$ (95:5, 50 ml) and the Li/Al complex decomposed with dilute HCl (1M, 50 ml). The crude product was obtained by the addition of butan-1-ol (300 ml) and by successively washing the organic solution with $NaHCO_3$ aq (2×150 ml) and water (2×150 ml) followed by evaporation under reduced pressure. The product, 1-(3'-deoxy-β-D-ribofuranosyl)naphthalene (0.44 g, 17%) was isolated as a white crystalline solid after chromatography on silica gel (Merck, Art No. 9385) with eluant of $MeOH:CH_2Cl_2$ (1:9) and evaporation of the solvent in vacuo.

δ ($CD_3OD$, 200 MHz); 8.18 (1H,m,ArH), 7.82 (3H,m, ArH), 7.5 (3H,m,ArH), 5.54 (1H,d,H-1'),4.48 (1H,m,H-4'), 4.52 (1H,m,H-2'), 3.88 (2H,dd,2H-5') 1.93 (2H,m,2H-3'). M/S $(M+NH_4)^+$262, $(M+H)^+$ 244. mp. 145°–147° C.

c) Preparation of 1-(2',3'-Anhydro-β-D-ribofuranosyl) naphthalene 1-(β-D-ribofuranosyl)naphthalene [(5.0 g, 19.2 mmole) prepared as described by Ohrui, H; Kuzuhara, H.; Emote, S. Agr. Biol. Chem 1972, 36 (9), 1651] in acetonitrile (50 ml) was treated with acetonitrile:water (99:1) (5 ml) and 2-acetoxyisobutyryl chloride (13.0 g, 80 mmole) and heated at 80° C. for 1 hour. The reaction mixture was concentrated under reduced pressure and EtOAc (200 ml) added. The solution was sequentially washed with saturated $NaHCO_3$ aq (3×200 ml), and $H_2O$ (3×200 ml) and concentrated under reduced pressure after drying over $MgSO_4$. The resulting brown oil was taken up in MeOH (30 ml) and treated with sodium methoxide (2M, 30 ml) at ambient temperature for 16 hours. The crude product was obtained by stirring with Amberlite IRC 50 (5 g, 50 mg) for 16 hours and by removing the solvent in vacuo. The product 1-(2',3'-anhydro-β-D-ribofuranosyl)naphthalene (2.5 g, 54%), was isolated as a white solid by chromatography on silica gel (Merck Art No 9385) with elution by $Et_3N:MeOH:CH_2Cl_2$ (1:10:189)

δ (($CD_3)_2SO$, 200 MHz); 8.12, 7.93 and 7.58 (7H,m, ArH), 5.77 (1H,s,H-1'), 4.94 (1H,t,OH), 4.16 (1H,dd,H-4'), 4.13 (1H,d,H-2' or H-3'), 3.99 (1H,d,H-3' or H-2'), 3.5 (2H,m,2H-5').

C) Preparation of $C_{16}$-alkylene oligonucleotide (6)

1) Oligonucleotide preparation

The fully protected oligodeoxyribonucleotide (6) was prepared as described in Preparation A1 except that position 5 on the Applied Biosystems DNA synthesiser contained a solution of N,N -diisopropylamino-[16-O-α,α-bis(p-methoxyphenyl)benzyl)hexadecan-1-O]methoxyphosphine [72 mg prepared as described in 1a below] in acetonitrile:1,2-dichloroethane (3:2) (1 ml) and the C-16 phosphoramidite was coupled by a standard coupling reaction used for normal phosphoramidites. The oligodeoxyribonucleotide was cleaved from the solid support, and 2 ml of concentrated ammonia added. Deprotection was carried out overnight at 55° C. in a waterbath. The oligonucleotide was dried under vacuum and resuspended in 1 ml of autoclaved deionised water (Milli Q) and stored at –20° C. ready for purification. 100 μl of the deprotected oligonucleotide was applied to an anion exchange column (Mono Q, Pharmacia) equilibrated with Buffer A (10 mM NaOH, 0.5M NaCl). Flow rate was set to 1 ml/min, chart speed 5 mm/min, Absorbance Scale 1.0 Fraction size 0.5 ml. The oligonucleotide was eluted with a gradient of Buffer B (10 mM NaOH, 0.9M NaCl) 0–100% in 60 minutes.

A number of small peaks eluted as the gradient increased followed by two larger peaks. Peak 1 corresponds approximately to a 30 mer (or less) whereas peak 2 corresponds to about a 60 mer. It is therefore probable that peak 2 contains the full length product. Fractions corresponding to each of the peaks were pooled (for each peak), separately concentrated by drying under vacuum and desalted, on a desalting and buffer exchange column (PD10, Pharmacia) ready for use.

Confirmation of the identity of the correct peak was determined by checking the purity of the oligodeoxyribonucleotides as described in Preparation A1, except that both peaks of oligonucleotide 6 were labelled. Autoradiography reveals that peak 2 represents the required oligodeoxyribonucleotide.

a) Preparation of N,N-Diisopropylamino-[16-O-α,α-bis(p-methoxyphenyl)benzyl)hexadecan- 1-O]methoxyphosphine 16-O-α,α-bis(p-methoxyphenyl)benzylhexadecan-1-ol prepared as described in 1b below] in $CH_2Cl_2$ (15 ml) was stirred with chloro(methoxy)-N-diisopropylphosphine (0.36 g, 1.79 mmole) in the presence of N,N-diisopropylethylamine (0.92 g, 7.2 mmole) at ambient temperature for 2 hours. The product, N-diisopropyl [16-O-α,α-bis(p-methoxyphenyl)benzyl hexadecan-1-O-]methoxyphosphine, (0.62 g, 48%) was isolated as a yellow oil by removing the solvent in vacuo and by chromatography on silica gel (Merck Art 9385) with eluant of Et₃N:hexane (1:9).

M/S 722 (M+H)⁺, δ (CDCl₃, 200 MHz); 7.3 and 6.8 (13H,m,Ar), 3.80 (6H,s,OCl₃), 3.59 (2H,m CH₂OP), 3.4 (3H,d,POCH₃), 3.03 (2H,t,CH₂ODMTr), 1.25 (42H,m,14C H₂, 2CH(CH₃)₂).

b) Preparation of 16-O-α,α-bis(p=methoxyphenyl)benzyl)hexadecan- 1-ol 1,16-Hexadecanediol (1.0 g, 3.8 mmole) was treated with α,α-bis(p-methoxyphenyl)benzyl chloride (1.28 g, 3.8 mmole) in pyridine (30 ml) at ambient temperature for 16 hours. The solvent was removed in vacuo and the product, 16-O-α,α-bis(p-methoxyphenyl)benzyl-hexadecan- 1-ol, (0.35 g, 16%) was isolated as a brown oil by flash chromatography on silica gel (Merck Art 9385) with eluant of MeOH:CH₂Cl₂ (1:99). M/S (M+H)⁺561

D) Preparation of oligonucleotide (8)

The fully protected oligodeoxyribonucleotide (8) was prepared as described in Preparation A1 above, except that position 5 on the Applied Biosystems DNA synthesiser contained a solution of the N,N-diisopropylaminomethylphosphoramidite of 5'-dimethoxytrityl- 2'-deoxythymidine (0.25 g) in anhydrous acetonitile (3.8 ml) and the methylphosphoramidite was coupled by a standard coupling reaction used for normal phosphoramidites. The procedures consisted briefly of: (1) removal of the α,α-bis(p-methoxyphenyl)benzyl group with 3% trichloroacetic acid in dichloromethane; (2) coupling of N,N-diisopropylaminomethylphosphoramidite of 5'-dimethoxytrityl-2'-deoxythymidine activated by tetrazole for 30 sec; (3) iodine oxidation of the intermediate phosphite to a phosphate; and (4) a capping step with acetic anhydride.

Alternatively, the fully protected oligodeoxyribonucleotide sequence may be prepared by the manual methods as described by Atkinson and Smith in 'Oligonucleotide Synthesis, a Practical Approach' (M. J. Gait Editor, IRL Press, Oxford, Washington D.C., pages 35–81). The detritylated oligodeoxyribonucleotide sequence was cleaved from the solid support and deprotected by treatment with ethylene diamine:ethanol (1:7 0.4 ml) at 55° C. for 55 minutes. The ethylene diamine in ethanol solution was evaporated at 50° C. under reduced pressure and the residue was treated again with the ethylene diamine:ethanol solution at 55° C. for 55 minutes. After a second evaporation under reduced pressure the residue was dissolved in water (1 ml). An aliquot of the solution containing the oligodeoxyribonucleotide was purified by polyacrylamide gel electrophoresis as described in Preparation A1.

EXAMPLE 2

This example demonstrates the ability of as little as one modified base to prevent polynucleotide tail amplification. The following oligonucleotides were prepared using methods analogous to those outlined in Example 1 above:
Oligonucleotide 2a;

AATTCCGTGCATAAGGCTGTGCTGNTC-
GACGAGAAAGGGACTGAAGCTGCTGGGGCCATG (where N is as described in oligonucleotide 2 in Example 1)

Oligonucleotide 4a;

AATTCCGTGCATAAGGCTGTGCTGNTC-
GACGAGAAAGGGACTGAAGCTGCTGGGGCCATG (where N is as described in oligonucleotide 3 in Example 1). Oligonucleotide 8a;

AATTCCGTGCATAAGGCTGTGCTGNTC-
GACGAGAAAGGGACTGAAGCTGCTGGGGCCATG (where N is as described in oligonucleotide 8 in Example 1).

The following reactions were then effected using procedures identical to those disclosed in Example 1:

|  |  |  | Length of product expected if bridge stops enzyme |  |
|---|---|---|---|---|
| a1) | Labelled 5 |  | 30 | (No template/no dNTPs) |
| a2) | Labelled 5 |  | 30 | (No template/no dNTPs) |
| a3) | Labelled 5 | + dNTPs (ACGT) | 30 | (No template/no extension) |
| b) | Labelled 5 | + 1 | 30 | (No dNTPs) |
| c) | Labelled 5 | + 2a | 30 | (No dNTPs) |
| d) | Labelled 5 | + 4a | 30 | (No dNTPs) |
| e) | Labelled 5 | + 8a | 30 | (No dNTPs) |
| f) | Labelled 5 | + 1 + dNTPs (ACGT) | 63 | Control |
| g) | Labelled 5 | + 2a + dNTPs (AGCT) | 35 |  |
| h) | Labelled 5 | + 4a + dNTPs (AGCT) | 35 |  |
| i) | Labelled 5 | + 8a + dNTPs (AGCT) | 35 |  |

Figure 2:
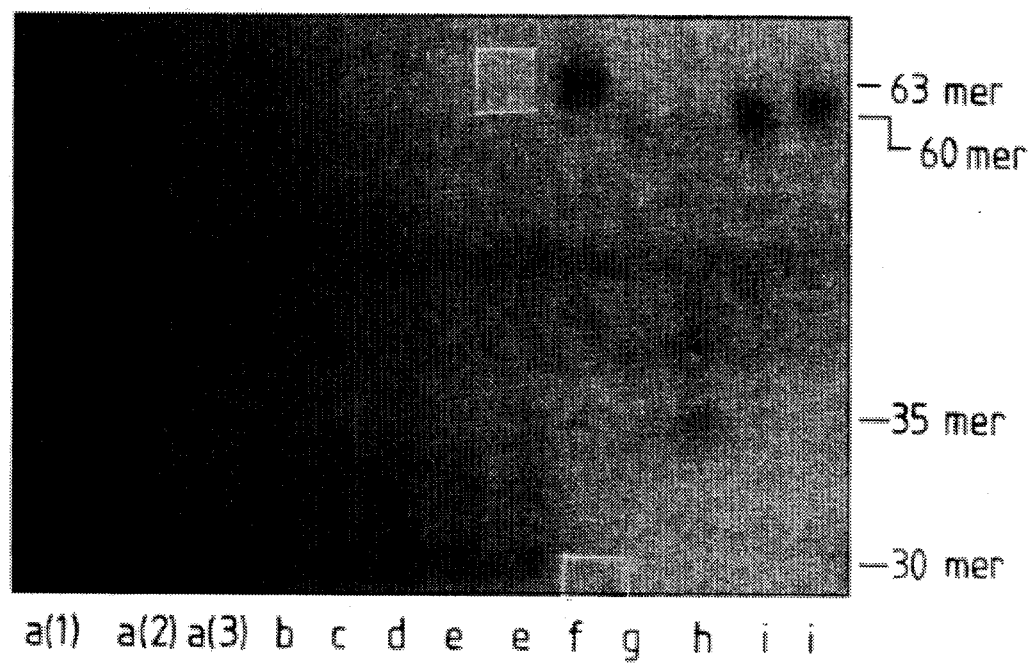
FIG. 2 is a representation of an autoradiograph showing the results of using single deoxyribofuranosyl and methyl phosphonate polymerisation blocking moieties in primers employed in the method of the present invention.

The results are shown in FIG. 2 and demonstrate that a single 3' deoxynaphthalene residue will stop extension by Taq DNA polymerase, a single 2' deoxynaphthalene will partially stop extension by Taq DNA polymerase and a single 4-methyl phosphonate substituted thymidine residue is ineffective in stopping extension by Taq DNA polymerase.

EXAMPLE 3

This example demonstrates the use of metaphosphate and thymidine phosphoramidate polymerisation blocking moieties to prevent polynucleotide tail amplification.

The following oligonucleotides were prepared:
Oligonucleotide 20;

AATTCCGTGCATAAGGCTGTGCT-
GNNNNTCGACGAGAAAGGGACTGAAGCT-
GCTGGGGCCATG wherein N represents a thymidine phosphormorpholidate group
Oligonucleotide 21;

AATTCCGTGCATAAGGCTGTGCTGNTC-
GACGAGAAAGGGACTGAAGCTGCTGGGGCCATG wherein N represents a thymidine phosphormorpholidate group
Oligonucleotide 22;

AATTCCGTGCATAAGGCTGTGCTGNTC-
GACGAGAAAGGGACTGAAGCTGCTGGGGCCATG wherein N represents a metaphosphate group
Oligonucleotide 23;

AATTCCGTGCATAAGGCTGTGCT-
GNNNTCGACGAGAAAGGGACTGAAGCT-
GCTGGGGCCATG wherein N represents a metaphosphate group Preparation of metaphosphate linked oligonucleotide sequences (a) The fully protected oligonucleotide of sequence:

5' AATTCCGTGCATAAGGCTGTGCTG N TCGACGAGAAGG-
GACTGAAGCTGCTGGGGCCATG 3' was prepared as described previously on an Applied Biosystems 380 A DNA Synthesiser, except that position 5 contained a solution of N,N-diisopropylamino-O-cyanoethyl-O-tritylmercaptamoethylphosphine (52 mgs) (Sinha N. D, Biarnot J., McManus J., and Koster A., Nucleic Acids Research, 1984, 12, 4539–4557) in anhydrous acetonitrile (1 ml). The phosphoramidite at position 5 was coupled to the oligonucleotide bound to a controlled pore glass support by the standard procedures used for coupling normal phosphoramidites except that the trityl protecting group was removed by manual treatment with an aqueous solution of silver nitrate (0.25M, 1 ml) at ambient temperature for 16 hours and, after washing with distilled water (2×1 ml), by treatment with an aqueous solution of dithiothreitol (0.3M, 1 ml, pH8.3) at ambient temperature for 16 hours. After washing the supported oligonucleotide sequence with distilled water (2×1 ml) followed by drying under reduced pressure at 50° C. (5 minutes), the synthesis of the fully protected oligonucleotide sequences completed using a standard cyanomethylphosphoramidite cycle on the DNA Synthesiser.

The detritylated oligonucleotide sequences were cleaved from the solid support and all the protecting groups removed by treatment with aqueous ammonia solution (sp.gr. 0.88, 55° C. for 16 hours). After removal of the ammonia solution under reduced pressure at 50° C., the residue was dissolved in sterile water (1 ml) and the metaphosphate bridged oligonucleotides isolated by polyacrylamide gel electrophoresis.

(b) The fully protected oligonucleotide of sequence:

5' AATTCCGTGCATAAGGCTGTGCTG NNN TCGAC-
GAGAAAGGGACTGAAGCTGCTGGGGCCATG 3' was prepared as described in preparation (a) except that the phosphoramidite at position 5 (N,N-diisopropylamino-O-cyanoethyl-O-tritylmercaptoethlyphosphine) was used in three standard cyanoethylphosphoramidite cycles with manual removal of the trityl protecting group before each coupling reaction. The synthesis, cleavage from the solid support and the deprotection of the bridged oligonucleotide sequences was completed as described in preparation (a) and the trimetaphosphate bridged oligonucleotides were isolated by polyacrylamide gel electrophoresis.

Preparation of phosphormorpholidate linked oligonucleotide sequnces (c) The fully protected oligonucleotide of sequence:

5' AATTCCGTGCATAAGGCTCTGCTG N TCGAC-
GAGAAAGGGACTGAAGCTGCTGGGGCCATG 3' were prepared as described previously using a standard cyanoethylphophoramidite cycle on an Applied Biosystems 380A DNA Synthesiser, except that poition 5 contained a solution of 5'-dimethoxytrityl-3'-thymidine H-phosphonate (250 mg) in anhydrous acetonitile:pyridine (1:1, 6 ml) and H-phosphonate reagents and protocols (Oligonucleotide Synthesis with Hydrogen-Phosphonate Monomers, Applied Biosystems User Bulletin, No 44, Nov. 20, 1987) were used to incorporate the reagent at position 5 into the oligonucleotide sequence. The procedures consisted briefly of: (1) removal of the dimethoytrityl group with 7% dichloroacetic acid in dichloromethane (2) coupling of the 5'-dimethoxytrityl-3'-thymidine H-phosphonate activated with 1-adamantanecarbonyl chloride for 40 seconds (3) a capping step with isopropylphosphite and 1-adamantanecarbonyl chloride and (4) the manual oxidation of the H-phosphonate diester with a solution of freshly distilled morpholine (10%) in carbon tetrachloride for 5 minutes. After incorporation of the reagent at position 5 into the oligonucleotide sequence, the synthesis of the fully protected oligonucleotide sequences was completed using standard cyanoethylphophoramidite reagents and a standard cycle on the DNA synthesiser.

The detritylated oligonucleotide sequences were cleaved from the controlled pore glass support and the protecting groups removed by treatment with aqueous ammonia solution (sp.gr. 0.88, 55° C., 16 hours). After removal of the ammonia solution under reduced pressure at 50° C., the residue was taken up in sterile water (1 ml) and the phosphormorpholidate bridged oligonucleotides isolated by pholyacrylamide gel electrophoresis.

(d) The fully protected oligonucleotide of sequence:

5' AATTCCGTGCATAAGGCTGTGCTG NNNN TCGAC-
GAGAAAGGGACTGAAGCTGCTGGGGCCATG 3' was prepared as described in preparation (c) except that the detritylation, coupling and capping steps with 5-dimethoxytrityl-3'-thymidine H-phosphonate at position 5 on an Applied Biosystems 380A DNA Synthesiser were repeated a further three times before the manual oxidation of the four H-phosphonate linkages with morpholine in carbon tetrachloride (10% solution for 5 minutes). The synthesis of the oligonucleotide sequences were completed using normal cyanoethylphosphoramidite reagents and synthesis cycle and the detritylated oligonucleotide sequences were cleaved from the controlled pore glass support and deptrotected by standard treatment with ammonia solution (sp.gr. 0.88, 55° C., 16 hours). After removal of the ammonia solution (reduced pressure at 50° C.) and the addition of sterile water (1 ml), the tetraphosphormorpholidate bridged oligonucleotide was isolated by polacrylamide gel electrophoresis.

Isolation:

An aliquot of the solutions containing the oligodeoxyribonucleotides was purified by polyacrylamide gel electrophoresis as described in preparation A1.

The following reactions were then effected using procedures identical to those disclosed in Example 1:

| | | | Length of product expected if bridge stops enzyme | |
| --- | --- | --- | --- | --- |
| a) | Labelled 5 | + dNTPs | 30 | (No template/no extension) |
| b) | Labelled 5 | + 1 | 30 | (No dNTPs) |
| c) | Labelled 5 | + 631 | 30 | (No dNTPs) |
| d) | Labelled 5 | + 632 | 30 | (No dNTPs) |
| e) | Labelled 5 | + 652 | 30 | (No dNTPs) |
| f) | Labelled 5 | + 657 | 30 | (No dNTPs) |
| g) | Labelled 5 | + 1  + dNTPs (ACGT) | 63 | Control |
| h) | Labelled 5 | + 631 + dNTPs (AGCT) | 35 | |
| i) | Labelled 5 | + 652 + dNTPs (AGCT) | 35 | |
| j) | Labelled 5 | + 632 + dNTPs (AGCT) | 35 | |
| k) | Labelled 5 | + 657 + dNTPs (AGCT) | 35 | |

Figure 3:
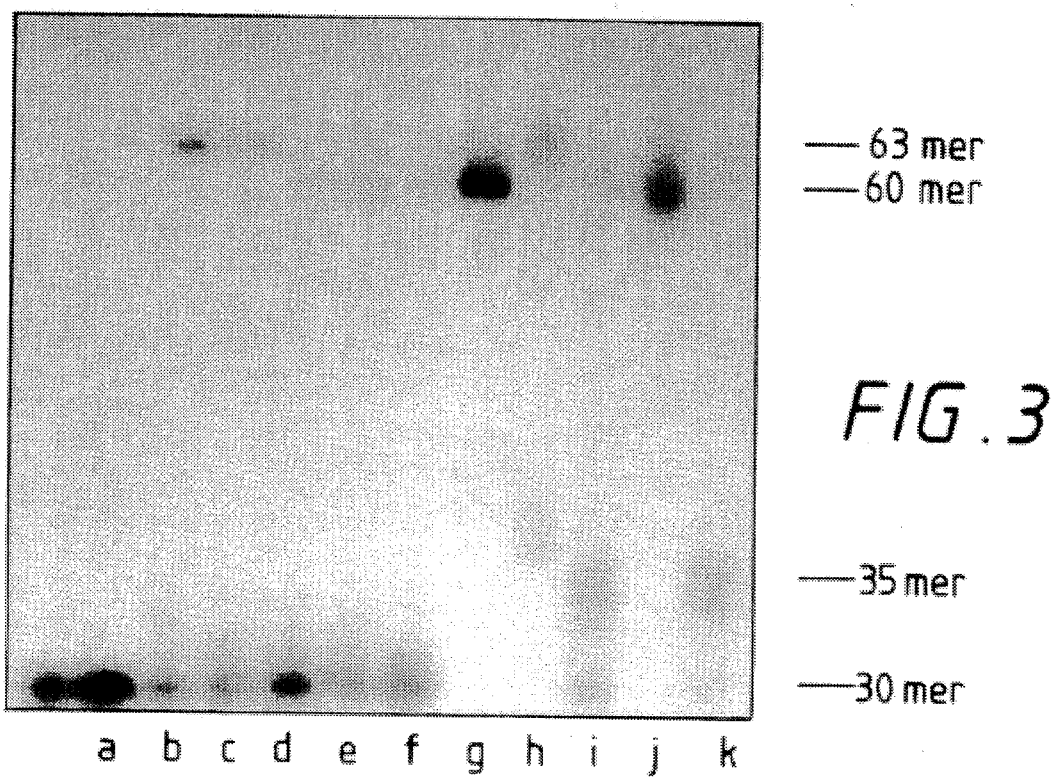
FIG. 3 is a representation of an autoradiograph showing the results of using phosphate and phosporamidate polymerisation blocking moieties in primers employed in the method of the present invention.

The results are shown in FIG. 3 and demonstrate that one and three metaphosphate moieties significantly inhibit extension by Taq DNA polymerase beyond the bridge. Four thymidine phosphormorpholidate moieties show useful blocking activity but a single thymidine phosphormorpholidate moiety shows negligible blocking activity.

Without wishing to be bound by any theoretical considerations the polymerase blocking activities may be underestimated because of the presence of the 63 mer bands in the controls with dNTPs omitted. The presence of these bands may be due to a carry over of polynucleotide kinase activity during combination of the template oligonucleotides with $^{32}P$ phosphorylated oligonucleotide 5.

EXAMPLE 4

This example demonstrates a microtitre plate test capture system to determine whether:

a) capture oligonucleotides are bound to a microtitre plate, b) there is nonspecific binding of the test capture oligonucleotide sequences to immobilised sequences other than their complement, or to the protein coating on the microtitre wells.

c) an alkaline phosphatase, nitro blue tetrazolium/5-bromo-4-chloro-3-indoyl phosphate p-toluidine salt (AP/NBT/BCIP) colour development system performs satisfactorily with the above capture oligonucleotides.

Capture oligonucleotides

Oligonucleotide 13; TTTTTTTTTTTATCAACTTACTTGCCTATA

Oligonucleotide 14; TTTTTTTTTTAGATCTTGGTTAACAATCGT

Oligonucleotide 15; TTTTTTTTTTCGGTCCTCATAATACATACT these are used as capture oligonucleotides for complementary hybridisation with oligonucleotides 11, 12 and 10 respectively as set out in Example 5 below. Oligonucleotide 13 is identical to olgionucleotide 7 as disclosed in Example 1. The 5'(dT)10 residues were included as spacer elements between the hybridisation regions and their respective conjugants.

These oligonucleotides were immobilised on protein coated microtitre plates as follows with reference to FIG. 4:

| Oligonucleotide 15 | A1 | B1 | C1 | D1 | E1 | F1 |
| Oligonucleotide 14 |    | B2 |    | D2 |    | F2 |
| Oligonucleotide 13 | A2 |    | C2 |    | E2 |    |
| No oligonucleotide | A3 | B3 | C3 | D3 | E3 | F3 |

The chosen concentration was such that 100% binding represents 1 nmole oligonucleotide per well.

Test capture oligonucleotides

Each oligonucleotide is a unique sequence, complementary to one of the capture oligonucleotides described above, and conjugated to the enzyme alkaline phosphatase (AP) using the E-link™ oligonucleotide labelling kit (Cambridge Research Biochemicals). The labelling was carried out with a nominal concentration of each oligonucleotide (1.5 μM).

Oligonucleotide 16;

TTTTTTTTTTAGTATGTATTATGAGGACCG

Oligonucleotide 17;

TTTTTTTTTTTATAGGCAAGTAAGTTGATA

Oligonucleotide 18;

TTTTTTTTTTACGATTGTTAACCAAGATCT these are used as capture control oligonucleotides Experimental details 200 μl of prehybridisation solution, containing 0.6M NaCl, 20 mM sodium phosphate pH 7.5, 1 mM EDTA, 0.02% Ficoll, 0.02% polyvinylpyrrolidine and 0.02% bovine serum albumin, was added to each well and incubated in the dark at 37° C. minutes. This was then removed by pipetting. The appropriate oligonucleotide enzyme conjugate was diluted 1 in 10 in a polymerase chain reaction (PCR) mix (100 μM dATP, 100 μM dGTP, 100 μM dCTP & 100 μM dTTP), 1.2mM $MgCl_2$, 50 mM KCl, 10 mM Tris HCl pH 8.3, 0.01% gelatine) and 10 μl of diluted conjugate, ie. approximately 1.5 pmoles were added to 40 μl of 5× SSC (1.1M NaCl, 0.825M sodium citrate pH 7.0 already added to each well). This was allowed to incubate in the dark at 37° C. for 1 hour. Solutions were then removed by pipetting. Each of the test capture control oligonucleotides was added to a different set of microtitre wells as prepared above and with reference to FIG. 4:

| Oligonucleotide 16 | A1 | A2 | A3 | B1 | B2 | B3 |
| Oligonucleotide 17 | C1 | C2 | C3 | D1 | D2 | D3 |
| Oligonucleotide 18 | E1 | E2 | E3 | F1 | F2 | F3 |

Following hybridisation, the wells were washed for 2×5 minutes at room temperature using 200 μl of 2× SSC (0.44M NaCl 0.33M sodium citrate pH 7.0). Solutions were again removed by pipetting.

The final step was addition of 200 μl of a colour development solution comprising alkaline phosphatase (AP) 9.5 buffer (0.1M Tris HCl pH 9.5, 0.1M NaCl, 5 mM $MgCl_2$) and containing NBT (0.33 mg/ml) and BCIP (0.17 mg/ml). The colour development solution was prepared as follows: for 15 ml of reagent, 5 mg of NBT was suspended in 1.5 ml AP 9.5 buffer in a microcentrifuge tube, vortexed vigorously for 1–2 minutes and then centrifgued briefly. The supernatant was decanted into 10 ml of AP 9.5 buffer, and warmed to 37° C. in a polypropylene tube. The residual NBT pellet was extracted twice more with 1.5 ml of AP 9.5 buffer and these supernatants pooled with the original solution. The tube was rinsed with a final 0.5 ml of AP 9.5 buffer and also decanted into the 15 ml NBT stock solution. BCIP (2.5 mg) was dissolved in 50 μl of N,N-dimethylformamide and added dropwise with gentle mixing into the NBT solution. The solution was frozen at −20° C. in 1 ml aliquots and then before use the solution was prewarmed to 37° C. in a water bath. Colour was allowed to develop in the dark at 37° C. and photographs were taken after 15 minutes and 2 hours 15 minutes.

Figure 4:
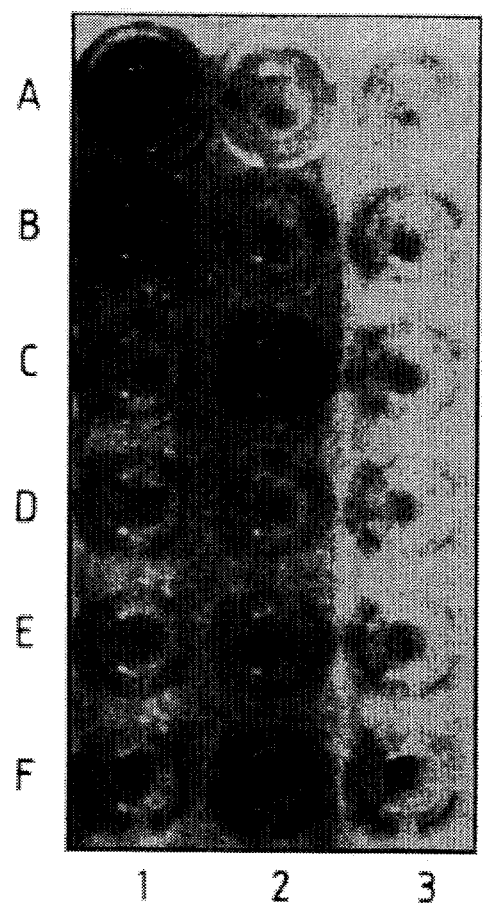
FIG. 4 is an illustration of the results obtained using a microtitre plate test capture system.
Figure 5:
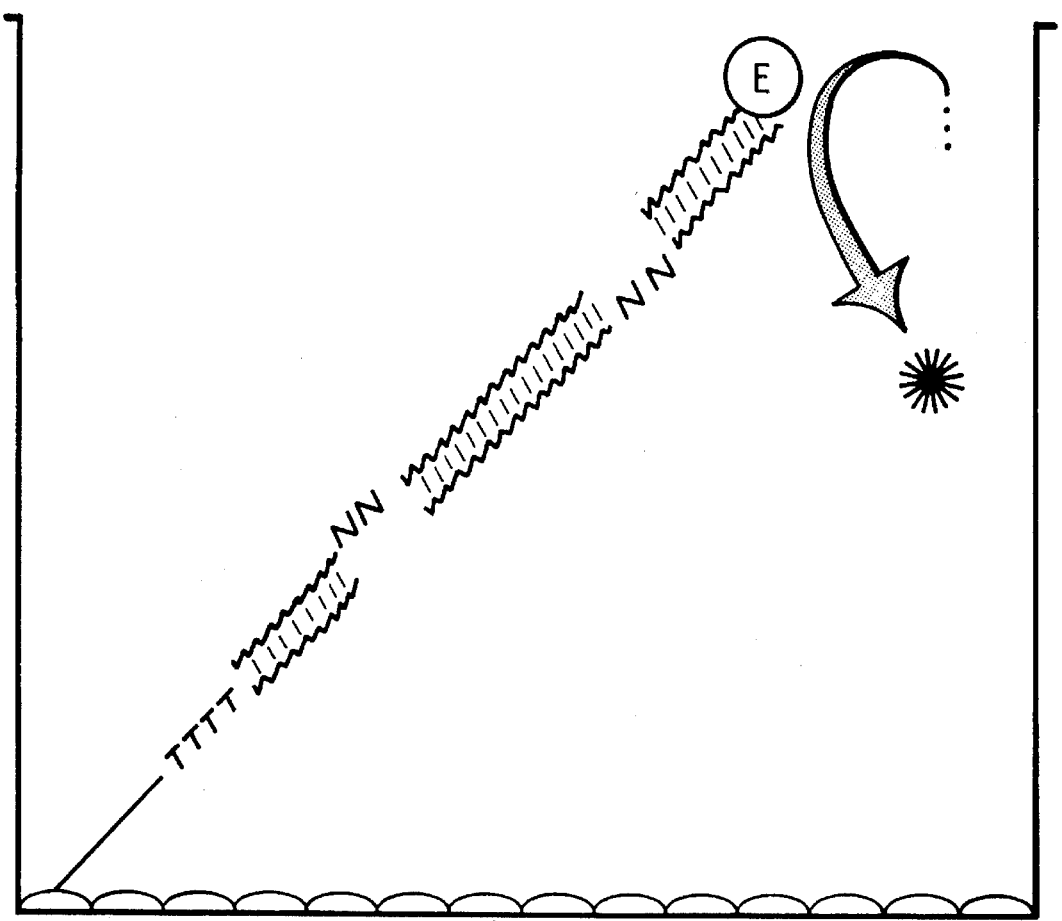
FIG. 5 illustrates a convenient assay format for performing the method of the present invention. The illustration shows one well of a microtitre plate with a protein coated internal surface. Immobilised on the internal surface is a solid phase capture oligonuclotide. The free end of this oligonucleotide is hybridised to a unique tail sequence on a double stranded amplification product. The other end of the PCR product likewise comprises a tail sequence which is hybridised to a signal oligonucleotide including an enzyme label represented by E. This label is used to react with a substrate leading to a detectable colour change as represented by the arrow and accompanying asterisk. NN represents a polymerisation blocking moiety which prevents formation of a double stranded tail.

The results are shown in FIG. 4 and show colour development only in wells A1 B1 C2 and F2 which is entirely consistent with the test capture oligonucleotides hybridising only to their complementary immobilised oligonucleotides under the conditions employed.

EXAMPLE 5

This example demonstrates the specific capture and detection of amplification products based on the S locus of the alpha-1-antitrypsin gene and using an internal amplification control based on sequence from exon V of the same gene. Detection of the immobilised products was achieved using an alkaline phosphatase (AP) conjugated common detection primer. This common primer was prepared using the E-link™ conjugation kit (Cambridge Research Biochemicals) as directed by the supplier and is complementary to the detection tail of all the amplified products.

The following oligonucleotides were used wherein N represents a 3'deoxyribofuranosyl naphthalene moiety, the naphthalene moieties being linked via the 2'-PO$_4$ grouping to the adjacent nucleotide:

Oligonucleotide 8b;

GTGTCGTCCCGCAGTCAATGNNNNC-
    CCACCTTCCCCTCTCTCCAGGCAAATGGG this oligonucleotide is the common signal primer for carrying out the ARMS assay method.

Oligonucleotide 9

GTGTCGTCCCGCAGTCAAT-
    GNNNNGAGACTTGGTATTTTGTTCAATCATTAAG

Oligonucleotide 10

AGTATGTATTATGAGGACCGNNNNTGTC-
    CACGTGAGCCTTGCTCGAGGCCTGGG these oligonucleotides are for the exon V control reaction and are the signal and capture primers respectively.

Oligonucleotide 11;

TATAGGCAAGTAAGTTGATANNNNTGGT-
    GATGATATCGTGGGTGAGTTCATTTT

Oligonucleotide 12;

ACGATTGTTAACCAAGATCTNNNNTGGT-
    GATGATATCGTGGGTGAGTTCATTTA oligonucleotides 11 and 12 are both capture primers and comprise respectively regions for complementary hybridisation to the published normal and mutant sequences of the S locus of the alpha-1-antitrypsin gene.

Oligonucleotide 13;

TTTTTTTTTTTATCAACTTACTTGCCTATA

Oligonucleotide 14;

TTTTTTTTTTAGATCTTGGTTAACAATCGT

Oligonucleotide 15;

TTTTTTTTTTCGGTCCTCATAATACATACT these are used as capture oligonucleotides for complementary hybridisation with oligonucleotides 11, 12 and 10 respectively. Oligonucleotide 13 is identical to oligonucleotide 7 as disclosed in Example 1. The 5'(dT)10 residues were included as spacer elements between the hybridisation regions and their respective conjugants.

Oligonucleotide 16;

TTTTTTTTTTAGTATGTATTATGAGGACCG

Oligonucleotide 17;

TTTTTTTTTTTATAGGCAAGTAAGTTGATA

Oligonucleotide 18;

TTTTTTTTTTACGATTGTTAACCAAGATCT these are used as capture control oligonucleotides Oligonucleotide 19;

TTTTTTTTTCATTGACTGCGGGACGACAC this is the common signal oligonucleotide for the ARMS assay method Preparation of oligonucleotides Oligonucleotides 13–15 and 16–19 were synthesised as 5' aminoalkyl derivatives using aminoalkyl phosphoramidite (Amino-link 2, Applied Biosystems) in the final synthesis cycle on the DNA synthesiser. These oligonucleotides were conjugated to alkaline phosphatase (AP) using the E-LINK™ oligonucleotide labelling kit as directed by the supplier (Cambridge Research Biochemicals).

Oligonucleotide purification

Aliquots of crude oligonucleotides 8b, 9, 10, 11 and 12 (225 µl) were precipitated by the addition of 25 µl of 3M sodium acetate pH 5.2, mixing and then adding 750 µl ethanol. After further mixing the tubes were left at −20° C. for one hour and spun for 10 minutes at 13,500 rpm before removing the supernatant. The pellets were left to air dry for 20 minutes then reconstituted with 50 µl formamide dye (80% formamide, 10 mM NaOH, 1 mM EDTA, 0.1% bromophenol blue). The samples were then loaded onto a 15% acrylamide gel in 7M urea, 100 mM Tris borate EDTA buffer pH 8.3, which had been prerun for 1 hour at 300 V. The samples were electrophoresed overnight at 140 V, ie. until the dye had run to the bottom of the gel (0.3×24×17 cm$^3$). The oligonucleotides were visualised by ultra violet shadowing at 254 nm on a 20×20 aluminium backed thin layer chromatography plate (Merck 5554) covered with Saran wrap. The bands were excised using a new scalpel for each band to prevent cross-contamination. The gel slices were placed separately into a length of treated dialysis tubing (boiled in 1 mM EDTA for ten minutes then rinsed 3× by boiling in milli Q water) containing 1 ml 10 mM Tris borate EDTA buffer pH 8.3. The oligonucleotides were electroeluted from the gel slice at 2100 V for 1.5 hours, the polarity was then reversed for 45 seconds. The eluates were removed into 1.5 ml quartz spectrophotometer cuvettes, the optical density at 220–330 nanometers was then scanned against the elution buffer and the concentration of oligonucleotide calculated based on the optical density at 260 nm. The oligonucleotides were then concentrated by butanol extraction until the volume of the aqueous layer was ~500 µl. A phenol chloroform 1:1 (500 µl) extraction was included. The aqueous phase was removed and further concentrated by butanol extraction to ~50 µl. This was then dried under vacuum and reconstituted with filtered MilliQ water to 50 pmoles/µl ready for the amplification reactions.

Thiolation of capture oligonucleotides 13, 14 & 15

The capture oligonucleotides (200 µl, 0.2 µMol synthesis) were mixed separately with 4 mg/ml iminothiolane in 0.2M Na$_2$CO$_3$/HCO$_3$ pH 9.6 (300 µl) and incubated at ambient temperature for 1 hour. The reactions were diluted to 1 ml with phosphate buffered saline (PBS) and desalted on a Nap-25 column (Pharmacia). The columns were washed with PBS (2.2 ml). The first 1.6 ml eluted was retained and the oligonucleotide concentrations were measured by u.v. spectrometry.

Immobilisation of thiolated oligonucleotides to microtitre dishes

Oligonucleotide immobilisation to microtitre wells was performed using a modification of the method described by Running, J. A. and Urdea, M. S., (1990), Biotechniques, 8, 276–277. Poly (Phe-Lys) (Sigma) was dissolved to 100 µg/ml in 50 mM Na$_2$CO$_3$/HCO$_3$, pH 9.6 and 100 µl of this solution was added to each well of five clear polystyrene microtitre dishes (Nunc). The dishes were incubated overnight at 4° C. then washed 3 times with PBS/0.05% Tween. Succinimidyl 4-(N-maleimidomethyl)cyclohexane-1-carboxylate (SMCC) was dissolved at 8.7 mg/ml in dry dimethylformamide and this solution was diluted 10 times with conjugation buffer (100 mM triethanolamine HCl, 1 mM $MgCl_2$, 1 mM $ZnSO_4$, pH 7.4). 100 µl of this solution was added to each microtitre well and the plates were incubated at ambient temperature for 1 hour. The wells were washed 5 times with water. Thiolated oligonucleotides, 10 µM in PBS, were added to appropriate microtitre wells at a rate of 100 µl per well. These were incubated overnight at 4° C. The wells were washed twice with PBS/0.05% Tween, twice with 5% lactose, 0.5% gelatin, 0.1% $N_3Na$, 6 mM PBS, pH 7.5. Finally the coated dishes were dried overnight in a laminar flow cabinet. The dishes were stored at 4° C. in vacuo.

Generation of PCR products with non amplifiable tails

ARMS analysis of a homozygous S variant of the alpha-1-antitrypsin gene:

1 µl DNA was added to a tube containing 1.2 mM $MgCl_2$, 50 mM KCl, 10 mM Tris HCl pH 8.3, 0.01% gelatin, and 100 µM dATP, 100 µM dGTP, 100 µM dCTP & 100 µM dTTP to make a reaction volume of 98 µl to a final concentration of 100 µM each and 50 p moles each of oligonucleotides 8b, 9, 10 and 11 (the ARMS primer specific for the normal allele). 1 µl DNA was also added to a similar tube containing oligonucleotide 12 (the ARMS primer specific for the S variant allele) instead of oligonucleotide 11. 2 drops of mineral oil were added to each tube and spun for 1 minute at 13500 rpm. The tubes were transferred into a PCR machine (Techne) where they were denatured at 95° C. for 5 minutes before 2 units of Taq polymerase (Perkin Elmer, Ampli-Taq) were added still at 95° C. to make the final volume 100 µl. The Techne machine was switched into the 2 step PCR programme of 2 minutes at 94° C., 4 minutes at 60° C., 35 cycles with a final 9.9 minutes extension step at 60° C. A 20 µl aliquot of the reaction mixtures was electophoresed on 1.5% agarose gel. This was to ascertain the genotype of the DNA sample by traditional analytical methods.

Figure 6:
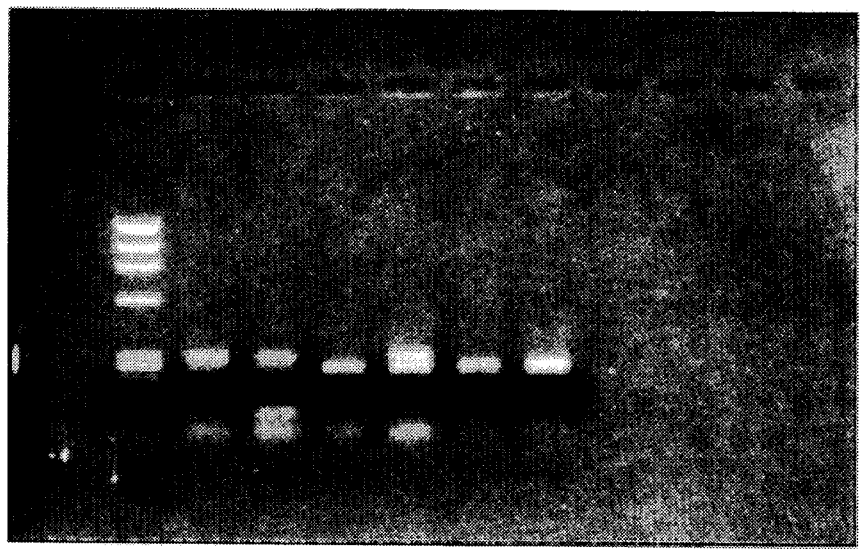
FIG. 6 illustrates the generation of PCR products in an allele specific amplification (ARMS) assay of the S locus of the alpha-1-antitrypsin gene.

The results are shown in FIG. 6:

| Lane 4 | S normal allele specific ARMS primer |
| Lane 5 | S variant allele specific ARMS primer |

The control (lower band) is present in both lanes whereas there is only a product band in lane 5 (S variant). This confirms that the DNA is from a homozygote for the S variant allele of the alpha-1-antitrypsin gene.

Solid phase capture and detection of ARMS products

Oligonucleotide 19, the common signal primer was econjgated to alkaline phosphatase using the E-link™ oligonucleotide labelling kit (Cambridge Research Biochemicals). The solutions are the same as those described in detail in Example 4 above unless otherwise stated:

1. 200 µl prehybridisation solution was added to each well. This was then incubated at 37° C. with shaking for 30 minutes. The solution was removed by pipetting.

2. A 20 µl aliquot of PCR product from the S normal primer tube was added to wells [A1, A2 and A3 with reference to FIG. 7] containing 60 µl 5× SSC. A 20 µl aliquot of PCR product from the S variant primer tube was added to wells [B1, B2 and B3 with reference to FIG. 7] also containing 60 µl 5×SSC. Hybridisation lasted for 1 hour at 37° C. with shaking. The solutions were then removed by pipetting.

Signal generation was as described in Example 4.

3. 10 µl diluted conjugated oligonucleotide 19 ie. ~1.5 pmoles was added to 40 µl 5× SSC already added to each well. Hybridisation lasted for 1 hour at 37° C. with shaking. The solutions were removed by pipetting.

4. 2×5 minutes washes with 200 µl 2× SSC at 37° C. were carried out with shaking. The solutions were removed by pipetting.

Figure 7:
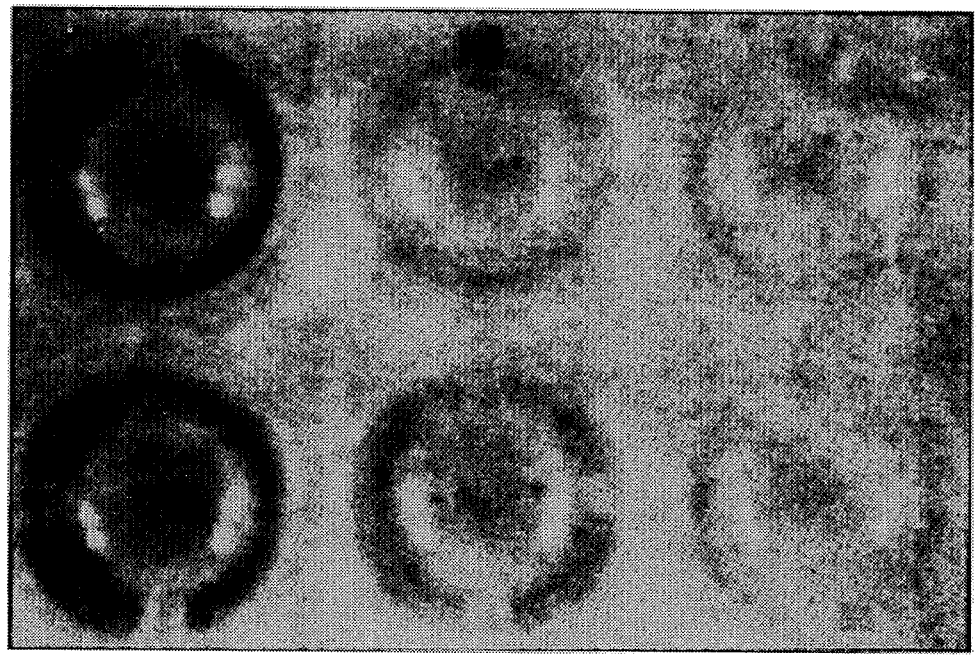
FIG. 7 illustrates the microtitre well arrangement for the above ARMS assay of the S locus of the alpha-1-antitrypsin gene and using an internal control based on exon V of the alpha-1-antitrypsin gene.

5. 200 µl of colour development solution was added to each well [A1, A2, A3, B1, B2 and B3 with reference to FIG. 7] and these were incubated for ~1 hour at 37° C. with shaking. The wells were then scanned using a Hewlett Packard Scan Jet Plus scanner and digitised using Apple Mackintosh software.

The results are shown in FIG. 7. It can be seen that both the internal control wells A1 and B1 are coloured. In addition only the variant well B2 is coloured providing a clear diagnosis that the DNA is from a homozygous S variant of alpha-1-antitrypsin. There is no significant non-specific binding, ie. there is no colour in the control wells A3 and B3.

The sequence identities 1–23 set out on the following pages correspond respectively to oligonucleotides 1–23 as hereinbefore described:

| SEQUENCE LISTING |
|---|

(1) GENERAL INFORMATION (i)    APPLICANT: Imperial Chemical Industries PLC (ii)   TITLE OF INVENTION: AMPLIFICATION PROCESSES (iii)  NUMBER OF SEQUENCES: 27

(iv)  CORRESPONDENCE ADDRESS:
        (A)   ADDRESSEE: Legal Department: Patents
        (B)   STREET: Bessemer Road
        (C)   CITY: Welwyn Garden City
        (D)   STATE: Hertfordshire
        (E)   COUNTRY: United Kingdom
        (F)   ZIP: GB-AL7 1HD (v)   COMPUTER READABLE FORM:
        (A)   MEDIUM TYPE: Diskette, 5.25 inch, 1.2 Mb storage
        (B)   COMPUTER: Tandon
        (C)   OPERATING SYSTEM: PC-DOS 3.20

SEQUENCE LISTING (D)    SOFTWARE: ASCII from WPS-PLUS (vi)    CURRENT APPLICATION DATA:
    (A)    APPLICATION NUMBER
    (B)    FILING DATE:

(vii)    PRIOR APPLICATION DATA:
    (A)    APPLICATION NUMBERS: GB 8920097.6
    (B)    FILING DATE: 06-SEP-1989

SEQ ID No 1
SEQUENCE LENGTH:    63
SEQUENCE TYPE:    Nucleotide
STRANDEDNESS:    Single
TOPOLOGY:    Linear
AATTCCGTGC ATAAGGCTGT GCTGACCATC GACGAGAAAG GGACTGAAGC TGCTGGGGCC    60
ATG    63

SEQ IN No 2
SEQUENCE LENGTH:    63
SEQUENCE TYPE:    Nucleotide
STRANDEDNESS:    Single
TOPOLOGY;    Linear
N:    2'-deoxyribofuranosyl naphthalene
AATTCCGTGC ATAAGGCTGT GCTGNNNNTC GACGAGAAAG GGACTGAAGC TGCTGGGGCC    60
ATG    63

SEQ IN No 2a
SEQUENCE LENGTH:    60
SEQUENCE TYPE:    Nucleotide
STRANDEDNESS:    Single
TOPOLOGY:    Linear
N:    2'-deoxyribofuranosyl naphthalene
AATTCCGTGC ATAAGGCTGT GCTGNTCGAC GAGAAAGGGA CTGAAGCTGC TGGGGCCATG    60

SEQ ID No 3
SEQUENCE LENGTH:    61
SEQUENCE TYPE:    Nucleotide
STRANDEDNESS:    Single
TOPOLOGY:    Linear
N:    2'-deoxyribofuranosyl naphthalene
AATTCCGTGC ATAAGGCTGT GCTGNNTCGA CGAGAAAGGG ACTGAAGCTG CTGGGGCCAT    60
G    61

SEQ ID No 4
SEQUENCE LENGTH:    63
SEQUENCE TYPE:    Nucleotide
STRANDEDNESS:    Single
TOPOLOGY:    Linear
N:    3'-deoxyribofuranosyl naphthalene
AATTCCGTGC ATAAGGCTGT GCTGNNNNTC GACGAGAAAG GGACTGAAGC TGCTGGGGCC    60
ATG    63

SEQ ID No 4a
SEQUENCE LENGTH:    60
SEQUENCE TYPE:    Nucleotide
STRANDEDNESS:    Single
TOPOLOGY:    Linear
N:    3'-deoxyribofuranosyl
AATTCCGTGC ATAAGGCTGT GCTGNTCGAC GAGAAAGGGA CTGAAGCTGC TGGGGCCATG    60

SEQ ID No 5
SEQUENCE LENGTH:    30
SEQUENCE TYPE:    Nucleotide
STRANDEDNESS:    Single
TOPOLOGY:    Linear
N:    2'-deoxyribofuranosyl naphthalene
CATGGCCCCAGCAGCTTCAGTCCCTTTCTC    30

SEQ ID No 6
SEQUENCE LENGTH:    60
SEQUENCE TYPE:    Nucleotide
STRANDEDNESS:    Single
TOPOLOGY:    Linear
N:    C4 straight chain alkylene
AATTCCGTGC ATAAGGCTGT GCTGNNNNTC GACGAGAAAG GGACTGAAGC TGCTGGGGCC    60
ATG    63

SEQUENCE LISTING

```
SEQ ID No 7
SEQUENCE LENGTH:    30
SEQUENCE TYPE:      Nucleotide
STRANDEDNESS:       Single
TOPOLOGY:           Linear
TTTTTTTTTT TATCAACTTA CTTGCCTATA                                        30

SEQ ID No 8
SEQUENCE LENGTH:    63
SEQUENCE TYPE:      Nucleotide
STRANDEDNESS:       Single
TOPOLOGY:           Linear
N:                  thymidine 4-methyl phosphonate
AATTCCGTGC ATAAGGCTGT GCTGNNNNTC GACGAGAAAG GGACTGAAGC TGCTGGGGCC       60
ATG                                                                     63

SEQ ID No 8a
SEQUENCE LENGTH:    60
SEQUENCE TYPE:      Nucleotide
STRANDEDNESS:       Single
TOPOLOGY:           Linear
N:                  thymidine 4-methyl phosphonate
AATTCCGTGC ATAAGGCTGT GCTGNTCGAC GAGAAAGGGA CTGAAGCTGC TGGGGCCATG       60

SEQ ID No 8b
SEQUENCE LENGTH:    54
SEQUENCE TYPE:      Nucleotide
STRANDEDNESS:       Single
TOPOLOGY:           Linear
N:                  3'-deoxyribofuranosyl naphthalene
GTGTCGTCCC GCAGTCAATG NNNNCCCACC TTCCCCTCTC TCCAGGCAAA TGGG             54

SEQ ID No 9
SEQUENCE LENGTH:    53
SEQUENCE TYPE:      Nucleotide
STRANDEDNESS:       Single
TOPOLOGY:           Linear
N:                  3'-deoxyribofuranosyl naphthalene
GTGTCGTCCC GCAGTCAATG NNNNGAGACT TGGTATTTTG TTCAATCATT AAG              53

SEQ ID No 10
SEQUENCE LENGTH:    54
SEQUENCE TYPE:      Nucleotide
STRANDEDNESS:       Single
TOPOLOGY:           Linear
N:                  3'-deoxyribofuranosyl naphthalene
AGTATGTATT ATGAGGACCG NNNNTGTCCA CGTGAGCCTT GCTCGAGGCC TGGG             54

SEQ ID No 11
SEQUENCE LENGTH:    54
SEQUENCE TYPE:      Nucleotide
STRANDEDNESS:       Single
TOPOLOGY:           Linear
N:                  3'-deoxyribofuranosyl naphthalene
TATAGGCAAG TAAGTTGATA NNNNTGGTGA TGATATCGTG GGTGAGTTCA TTTT             54

SEQ ID No 12
SEQUENCE LENGTH:    54
SEQUENCE TYPE:      Nucleotide
STRANDEDNESS:       Single
TOPOLOGY:           Linear
N:                  3'-deoxyribofuranosyl naphthalene
ACGATTGTTA ACCAAGATCT NNNNTGGTGA TGATATCGTG GGTGAGTTCA TTTA             54

SEQ ID No 13
SEQUENCE LENGTH:    30
SEQUENCE TYPE:      Nucleotide
STRANDEDNESS:       Single
TOPOLOGY:           Linear
TTTTTTTTTT TATCAACTTA CTTGCCTATA                                        30

SEQ ID No 14
SEQUENCE LENGTH:    30
SEQUENCE TYPE:      Nucleotide
STRANDEDNESS:       Single
TOPOLOGY:           Linear
TTTTTTTTTT AGATCTTGTT TAACAATCGT                                        30
```

SEQUENCE LISTING

```
SEQ ID No 15
SEQUENCE LENGTH:      30
SEQUENCE TYPE:        Nucleotide
STRANDEDNESS:         Single
TOPOLOGY:             Linear
TTTTTTTTTT CGGTCCTCAT AATACATACT                                          30

SEQ ID No 16
SEQUENCE LENGTH:      30
SEQUENCE TYPE:        Nucleotide
STRANDEDNESS:         Single
TOPOLOGY:             Linear
TTTTTTTTTT AGTATGTATT ATGAGGACCG                                          30

SEQ ID No 17
SEQUENCE LENGTH:      30
SEQUENCE TYPE:        Nucleotide
STRANDEDNESS:         Single
TOPOLOGY:             Linear
TTTTTTTTTT TATAGGCAAG TAAGTTGATA                                          30

SEQ ID No 18
SEQUENCE LENGTH:      30
SEQUENCE TYPE:        Nucleotide
STRANDEDNESS:         Single
TOPOLOGY:             Linear
TTTTTTTTTT ACGATTGTTA ACCAAGATCT                                          30

SEQ ID No 19
SEQUENCE LENGTH:      30
SEQUENCE TYPE:        Nucleotide
STRANDEDNESS:         Single
TOPOLOGY:             Linear
TTTTTTTTTT CATTGACTGC GGGACGACAC                                          30

SEQ ID No 20
SEQUENCE LENGTH:      63
SEQUENCE TYPE:        Nucleotide
STRANDEDNESS:         Single
TOPOLOGY:             Linear
N:                    thymidine phosphormorpholidate
AATTCCGTGC ATAAGGCTGT GCTGNNNNTC GACGAGAAAG GGACTGAAGC TGCTGGGGCC          60
ATG                                                                       63

SEQ ID No 21
SEQUENCE LENGTH:      60
SEQUENCE TYPE:        Nucleotide
STRANDEDNESS:         Single
TOPOLOGY:             Linear
N:                    thymidine phosphormorpholidate
AATTCCGTGC ATAAGGCTGT GCTGNTCGAC GAGAAAGGGA CTGAAGCTGC TGGGGCCATG          60

SEQ ID No 22
SEQUENCE LENGTH:      60
SEQUENCE TYPE:        Nucleotide
STRANDEDNESS:         Single
TOPOLOGY:             Linear
N:                    metaphosphate
AATTCCGTGC ATAAGGCTGT GCTGNTCGAC GAGAAAGGGA CTGAAGCTGC TGGGGCCATG          60

SEQ ID No 23
SEQUENCE LENGTH:      63
SEQUENCE TYPE:        Nucleotide
STRANDEDNESS:         Single
TOPOLOGY:             Linear
N:                    metaphosphate
AATTCCGTGC ATAAGGCTGT GCTGNNNTCG ACGAGAAAGG GACTGAAGCT GCTGGGGCCA          60
TG                                                                        62
```

I claim:

1. A method for the amplification of a target nucleotide sequence, which method comprises:

contacting the target nucleotide sequence under hybridising conditions, together or sequentially, with a first primer for a portion of said target nucleotide sequence, an amplification primer, nucleotides appropriate to said amplification, and an agent for polymerisation of the nucleotides, the first primer comprising:

1) a target binding nucleotide moiety which is substantially complementary to the portion of the target nucleotide sequence; and
2) a polynucleotide tail;

such that the first primer is subjected to primer extension whereby a first primer extension product is synthesised based on the target nucleotide sequence as template;

denaturing the first primer extension product from its template; and hybridising the amplification primer to a portion of the first primer extension product, whereby an amplification primer extension product is formed;

whereby the presence of the first primer in the first primer extension product is effective to inhibit formation in the amplification primer extension product of a sequence complementary to the polynucleotide tail.

2. A method as claimed in claim 1 wherein the amplification primer comprises:

1) a target binding nucleotide moiety which is substantially complementary to a portion of the first primer extension product; and 2) a polynucleotide tail;

and said method further comprises:

denaturing the amplification primer extension product from its template; and hybridising the first primer to a portion of the amplification primer extension product whereby a first primer extension product is formed;

whereby the presence of the amplification primer in the amplification primer extension product is effective to inhibit formation in the first primer extension product of a sequence complementary to the polynucleotide tail.

3. A method as claimed in claim 1 or 2 wherein either or both the first primer and the amplification primer comprise a target binding nucleotide moiety linked to a polynucleotide tail and wherein the target binding nucleotide moiety and the polynucleotide tail are in an opposite sense to one another.

4. A method as claimed in claim 1 or 2 wherein either or both of the first primer and the amplification primer comprise a target binding nucleotide moiety linked to more than one polynucleotide tail.

5. A method as claimed in claim 4 wherein each polynucleotide tail is linked to no more than one target binding nucleotide moiety.

6. A method as claimed in claim 1 or 2 wherein either or both the first primer and the amplification primer comprise a target binding nucleotide moiety and a polynucleotide tail with a nucleotide polymerisation blocking moiety therebetween.

7. A method as claimed in claim 6 wherein the nucleotide polymerisation blocking moiety comprises at least one ribofuranosyl naphthalene, deoxy ribofuranosyl naphthalene, metaphosphate or straight chain alkylene moiety or comprises at least two moieties independently selected from the group consisting of nucleotide methyl phosphonates and nucleotide phosphoramidates.

8. A method as claimed in claim 6 wherein the nucleotide polymerisation blocking moiety comprises at least two ribofuranosyl naphthalene, deoxy ribofuranosyl naphthalene or metaphosphate moieties, or comprises a C6-20 straight chain alkylene moiety.

9. A method as claimed in claim 1 or 2 wherein the polynucleotide tail of a primer in respect of a first target nucleotide sequence is distinguishable from the polynucleotide tail(s), in respect of further target nucleotide sequence(s) such that amplified product in respect of the first target nucleotide sequence is captured onto a first and distinguishable solid phase whilst amplified product(s) in respect of further target nucleotide sequence(s) are captured on one or more further solid phase(s).

10. A method as claimed in claim 1 or 2 wherein the amplified product in respect of a target nucleotide sequence is distinguishably labelled or marked via the primer's polynucleotide tail and the amplified product(s) in respect of further target nucleotide sequence(s) are also labelled or marked.

11. A method as in claim 1 or 2 wherein the first and further target nucleotide sequences correspond to alleles of a genetic locus.

12. A method as claimed in claim 1 or 2 wherein the target binding nucleotide moiety of either or both of the first primer and the amplification primer is exactly complementary to the desired portion of the target sequence or the first primer extension product, respectively.

13. A kit for the amplification of one or more target nucleotide sequences which comprises a first primer and an amplification primer for each target nucleotide sequence to be amplified, said first primer and amplification primer being capable of initiating, respectively, the synthesis of a first primer extension product and an amplification primer extension product, each first primer comprising:

1) a target binding nucleotide moiety which is substantially complementary to a portion of the target nucleotide sequence; and 2) a polynucleotide tail;

the first primer in the first primer extension product being effective to inhibit formation of a sequence in the amplification primer extension product complementary to the polynucleotide tail.

14. A kit as claimed in claim 13 wherein the amplification primer comprises:

1) a target binding nucleotide moiety which is substantially complementary to the desired portion of the target nucleotide sequence; and 2) a polynucleotide tail;

the amplification primer in the amplification primer extension product being effective to inhibit formation in a first primer extension product of a sequence complementary to the polynucleotide tail.

15. A kit as claimed in claim 13 which additionally comprises at least one solid phase carrying a nucleotide sequence with at least a portion thereof substantially complementary to the polynucleotide tail of at least one of said first primer and said amplification primer.

* * * * *